US012714350B2

(12) United States Patent
Houben et al.

(10) Patent No.: US 12,714,350 B2
(45) Date of Patent: Aug. 25, 2026

(54) MEDICAL APPARATUS FOR DIAGNOSTIC AND SITE DETERMINATION OF CARDIAC ARRHYTHMIAS AND METHODS

(71) Applicant: Biosense Webster (Israel) Ltd., Yokneam (IL)

(72) Inventors: Richard P.M. Houben, Lanaken (BE); Lior Botzer, Timrat (IL); Meir Bar-Tal, Haifa (IL); Milad El Haddad, Helsinki (FI); Frederick Geier Evans, Birmingham, AL (US); Zachary P Bubar, Cleveland, OH (US)

(73) Assignee: Biosense Webster (Israel) Ltd., Yokneam (IL)

(*) Notice: Subject to any disclaimer, the term of this patent is extended or adjusted under 35 U.S.C. 154(b) by 1186 days.

(21) Appl. No.: 17/706,223

(22) Filed: Mar. 28, 2022

(65) Prior Publication Data

US 2022/0369991 A1 Nov. 24, 2022

Related U.S. Application Data

(60) Provisional application No. 63/189,957, filed on May 18, 2021.

(51) Int. Cl.
*A61B 5/308* (2021.01)
*A61B 5/287* (2021.01)
(Continued)

(52) U.S. Cl.
CPC .............. *A61B 5/308* (2021.01); *A61B 5/287* (2021.01); *A61B 5/339* (2021.01); *A61B 5/349* (2021.01); *A61B 5/367* (2021.01); *A61B 18/12* (2013.01)

(58) Field of Classification Search
None
See application file for complete search history.

(56) References Cited

U.S. PATENT DOCUMENTS 6,748,255 B2 6/2004 Fuimaono
6,814,733 B2 11/2004 Schwartz
(Continued)

OTHER PUBLICATIONS

European Search Report for corresponding EPA No. 22173737.2 dated Sep. 14, 2022.
(Continued)

*Primary Examiner* — Kennedy Schaetzle
(74) *Attorney, Agent, or Firm* — Clayton, McKay & Bailey, PC

(57) ABSTRACT

Medical apparatus and methods for diagnostic and site determination of cardiac arrhythmias within a heart of a subject are provided. A computing device receives, records and processes electrocardiogram (ECG) signals in the form of bipolar and unipolar ECGs associated with respective cardiac tissue locations corresponding to catheter distal end sensors on locations. Unipolar ECGs that include signals from a plurality of successive heartbeats corresponding to locations within an area of study are analyzed to identify Fractionated Unipolar ECG Signal Complexes (FUESCs) of unipolar ECGs by defining complexes of the unipolar ECGs that correspond to respective bipolar activity windows. Identified arrhythmia sites for treatment include a predetermined number of unipolar ECGs that have a predetermined number of FUESCs. Atrial arrhythmia sites for treatment by ablation can be identified with respect to FUESCs of unipolar ECGs that include signals from at least ten successive heartbeats of an atrial tissue study area.

20 Claims, 24 Drawing Sheets

(51) Int. Cl.

| | |
|---|---|
| ***A61B 5/339*** | (2021.01) |
| ***A61B 5/349*** | (2021.01) |
| ***A61B 5/367*** | (2021.01) |
| ***A61B 18/12*** | (2006.01) |

(56) References Cited

U.S. PATENT DOCUMENTS

| | | | | |
|---|---|---|---|---|
| 6,961,602 | B2 | 11/2005 | Fuimaono | |
| 6,997,924 | B2 | 2/2006 | Schwartz | |
| 7,156,816 | B2 | 1/2007 | Schwartz | |
| 7,536,218 | B2 | 5/2009 | Govari | |
| 7,756,576 | B2 | 7/2010 | Levin | |
| 9,380,953 | B2 | 7/2016 | Houben | |
| 2003/0023130 | A1 | 1/2003 | Ciaccio et al. | |
| 2007/0197929 | A1 | 8/2007 | Porath et al. | |
| 2014/0235988 | A1* | 8/2014 | Ghosh | A61B 5/361 600/374 |
| 2015/0208942 | A1 | 7/2015 | Bar-Tal | |
| 2015/0313491 | A1* | 11/2015 | Edwards | G16Z 99/00 600/509 |
| 2016/0051160 | A1 | 2/2016 | Harlev et al. | |
| 2017/0202470 | A1* | 7/2017 | Urman | A61B 5/316 |

OTHER PUBLICATIONS

Three-Dimensional Mapping of Cardiac Arrhythmias—What Do the Colors Really Mean?, Munoz et al., Circulation: Arrhythmia and Electrophysiology, 2010, vol. 3, Issue 6: e6-e11, originally published Dec. 1, 2010, https://doi.org/10.1161/CIRCEP.110.960161.

* cited by examiner

Complex start, end, duration {CS, CE, CD}
Max amplitude, slope {CA, CV}
Number of slopes {CN}

CAR = min(CA)/max(CA) CSR = min(CS) /max(CS)

MEDICAL APPARATUS FOR DIAGNOSTIC AND SITE DETERMINATION OF CARDIAC ARRHYTHMIAS AND METHODS

CROSS REFERENCE TO RELATED APPLICATION

This application claims the benefit of U.S. provisional application No. 63/189,957 filed May 18, 2021, which is incorporated by reference as if fully set forth.

FIELD OF INVENTION

This invention relates to the diagnosis and treatment of cardiac arrhythmias. More particularly, this invention relates to obtaining information indicative of regional electrical activity in the cardiac chambers, and to the identification and treatment of arrhythmogenic areas.

BACKGROUND

Cardiac arrhythmias such as atrial fibrillation are a group of conditions in which the heart beats too fast, too slow, or with an irregular rhythm. Arrhythmias are the cause of death for approximately 300,000 people worldwide each year. Some patients with serious arrythmias are not successful with drug therapy, and so catheter ablation may be recommended and has been shown to reduce symptoms and improve patients' quality of life.

Electrical mappings of a patient's heart may serve as the basis for deciding on a therapeutic course of action, such as tissue ablation, to alter the propagation of the heart's electrical activity and to restore normal heart rhythm. Electrical properties of heart tissue, such as local activation time, may be measured as a function of the precise location within the heart. Data may be acquired using one or more catheters having electrical and location sensors in their distal tips which are advanced into the heart. Electrical activity at a point in the heart is typically measured by advancing a catheter comprising an electrical sensor at or near its distal tip to the point in the heart, contacting the tissue with the sensor, and acquiring data at the point. Multiple-electrode catheters have been developed to simultaneously measure electrical activity at multiple points in the heart chamber. Data may be accumulated at 100 or more sites to generate a detailed cardiac mapping.

Over the past decade, several mapping studies in human atrial fibrillation have made the important observations. Atrial electrograms during sustained atrial fibrillation have three distinct patterns: single potential, double potential, and complex fractionated atrial electrograms (CFAEs), based on discrete deflections per beat separated by an isoelectric interval or a low amplitude baseline. The CFAE areas represent atrial fibrillation substrate sites and may be target sites for treatment, such as ablation. By ablating areas having persistent CFAE's, atrial fibrillation may be eliminated or even rendered non-inducible.

It would be advantageous to have an improved fractionated detection system for faster and more reliable identification of target ablation sites. Currently, voltage and substrate maps are insufficient for identification of channel or isthmus sites that correspond to atrial flutter. An isthmus site, such as cavotricuspid isthmus, may be a target for ablation for treatment of atrial flutter. It would be advantageous to have a system that would provide for automatic identification of fractionated signals. It would also be advantageous for the system to determine which of the fractionated signals are related to channel or isthmus sites that correspond to atrial flutter.

SUMMARY

Medical apparatus and methods for diagnostic and site determination of cardiac arrhythmias within a heart of a subject are provided. A computing device receives, records and processes electrocardiogram (ECG) signals in the form of bipolar and unipolar ECGs associated with respective cardiac tissue locations based on sensing locations of catheter distal end sensors. Recorded unipolar ECGs that include signals from a plurality of successive heartbeats corresponding to locations within a cardiac tissue area of study are analyzed to identify Fractionated Unipolar ECG Signal Complexes (FUESCs) from among the unipolar ECGs by defining complexes of a unipolar ECG that correspond to respective bipolar activity windows. Cardiac arrhythmia sites identified for treatment by ablation include a predetermined number of unipolar ECGs that have a predetermined number of FUESCs.

Atrial arrhythmia sites for treatment by ablation can be identified with respect to FUESCs of unipolar ECGs from an atrial tissue study area that include signals from at least ten successive heartbeats.

In one example, a medical apparatus for diagnostic and site determination of cardiac arrhythmias within a heart of a subject has a catheter component including at least one catheter having a plurality of selectively locatable distal end sensors configured to sense (ECG) signals within the subject's heart coupled to a computing device having a processor and associated memory. The computing device is configured to receive, record and process electrocardiogram (ECG) signals in the form of bipolar and unipolar ECGs associated with respective cardiac tissue locations based on sensing locations of respective distal end sensors.

The processor configured to identify Fractionated Unipolar ECG Signal Complexes (FUESCs) from among the received unipolar ECGs with respect to a cardiac tissue area of study for which unipolar ECGs are recorded that include signals from a plurality of successive heartbeats corresponding to locations within the cardiac tissue area of study. The FUESCs are identified by determining bipolar activity windows from a bipolar ECG comprising a first unipolar ECG and a second unipolar ECG, defining a series of complexes of the first unipolar ECG that each correspond to a respective bipolar activity window, determining a plurality of complex level parameters with respect to the complexes of the first unipolar ECG with respect to a plurality of successive bipolar activity windows, calculating a plurality of complex level ratings based on at least one of the plurality of complex level parameters. calculating a quality of annotation measurement (QoA) with respect to the complexes of the first unipolar ECG using a plurality of parameters that include at least one of the plurality of complex level parameters and at least one of the plurality of complex level ratings, determining an evidence annotation measurement (EVI) with respect to the complexes of the first unipolar ECG using at least one of the plurality of complex level parameters and at least one of the plurality of complex level ratings, and calculating a final score with respect to the complexes of the first unipolar ECG based on the QoA and the EVI of each complex such that a complex of the first unipolar ECG is determined to be a FUESC upon a condition that its final score is at least a predetermined threshold.

In this example, the processor is configured to determine a cardiac arrhythmia site for treatment by ablation as a cardiac tissue site that includes respective locations corresponding to a predetermined number of unipolar ECGs that include a predetermined number of FUESCs.

The example apparatus may also include a display coupled with the computing device with the processor configured to output to the display a visualization of the cardiac tissue area of study of the subject's heart. Such output display may include:

- the relative locations of the distal end sensors with respect thereto along with selected sensed ECGs received by at least one of the distal end sensors;
- a visual indication of cardiac tissue determined to be cardiac arrhythmia sites for treatment by ablation; and/or
- a colorization of the cardiac tissue based on selected criteria.

The processor can be configured to determine the bipolar activity windows by determining a first activity window and a second activity window and fusing the first activity window and the second activity window on a condition that they overlap by 20 percent or more.

The example apparatus may determine a cardiac arrhythmia site for treatment by ablation where the unipolar ECGs include signals from at least ten successive heartbeats and the cardiac tissue area of study is atrial tissue of at least a portion of an atrial chamber of the subject's heart. In such case, the plurality of complex level parameters within the bipolar activity window that the processor is configured to determine may be selected from a group consisting of: complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV) and the processor is configured to determine an atrial cardiac arrhythmia site for treatment by ablation as an atrial tissue site that includes respective locations corresponding to at least three unipolar ECGs that include at least three successive of FUESCs.

The processor may be configured to calculate the plurality of complex level ratings using parameters selected from a group consisting of: number of slopes (CN), maximum amplitude (CA), maximum slope (CV), relative amplitude range (AREST), relative slope range (VREST), absolute amplitude range (ASCALE), and absolute slope range (VSCALE) and/or to calculate the QoA based on at least two parameters of the group consisting of: ASCALE, VSCALE, AREST, VREST, CAR, CVR, unipolar/bipolar slope overlap (UBO), CMS, CTS, and CDE. The processor may also be configured to determine a potential type of the complexes of the first unipolar electrogram as either a single potential, a double potential, a fractionated potential or a highly fractionated potential and to calculate QoA with respect to the complexes of the first unipolar ECG based on the formula:

$$QoA = 100 * \left(\sum_{i=1}^{N} P_i * w_{p,i}\right) \Big/ \sum w_{pi}$$

where N is the number of parameters, $P_i$ is the value of the ith of the N parameters listed above, $w_{p,i}$ is a weight value for the ith parameter depending on a potential type p.

The processor may also be configured to calculate the final score with respect to the complexes of the first unipolar ECG as a percentage of the sum of EVI plus M, where EVI is determined as a percentage based on a table entry corresponding to an amplitude scale, complex width, and amplitude ratio classification and a number of slopes and the potential type of the first unipolar ECG and M is calculated as a percentage value based on the formula:

$$M = \left[2 * \left(1 - \frac{EVI}{100}\right) * QoA\right] + (EVI - 100).$$

An example method for diagnostic and site determination of cardiac arrhythmias within a heart of a subject includes receiving, recording, and processing electrocardiogram (ECG) signals in the form of bipolar and unipolar ECGs associated with respective cardiac tissue locations based on sensing locations of respective distal end sensors of a catheter. Fractionated Unipolar ECG Signal Complexes (FUESCs) from among the recorded unipolar ECGs are identified with respect to a cardiac tissue area of study for which unipolar ECGs are recorded that include signals from a plurality of successive heartbeats corresponding to locations within the cardiac tissue area of study.

The FUESCs may be identified by:

- determining bipolar activity windows from a bipolar ECG comprising a first unipolar ECG and a second unipolar ECG and defining a series of complexes of the first unipolar ECG that each correspond to a respective bipolar activity window;
- determining a plurality of complex level parameters with respect to the complexes of the first unipolar ECG with respect to a plurality of successive bipolar activity windows;
- calculating a plurality of complex level ratings based on at least one of the plurality of complex level parameters;
- calculating a quality of annotation measurement (QoA) with respect to the complexes of the first unipolar ECG using a plurality of parameters that include at least one of the plurality of complex level parameters and at least one of the plurality of complex level ratings;
- determining an evidence annotation measurement (EVI) with respect to the complexes of the first unipolar ECG using at least one of the plurality of complex level parameters and at least one of the plurality of complex level ratings; and
- calculating a final score with respect to the complexes of the first unipolar ECG based on the QoA and the EVI of each complex such that a complex of the first unipolar ECG is determined to be a FUESC upon a condition that its final score is at least a predetermined threshold.

A cardiac tissue site that includes respective locations corresponding to a predetermined number of unipolar ECGs that include a predetermined number of FUESCs is determined to be cardiac arrhythmia site for treatment by ablation.

The method may include displaying a visualization of the cardiac tissue area of study of the subject's heart such as visualizations that include the relative locations of the distal end sensors with respect thereto along with selected sensed ECGs received by at least one of the distal end sensors, a visual indication of cardiac tissue determined to be cardiac arrhythmia sites for treatment by ablation, and/or a colorization of the cardiac tissue based on selected criteria.

The method may include determining the bipolar activity windows includes determining a first activity window and a second activity window and fusing the first activity window and the second activity window on a condition that they overlap by 20 percent or more.

The method may be conducted with respect to unipolar ECGs that include signals from at least ten successive heartbeats and a cardiac tissue area of study that is atrial tissue of at least a portion of an atrial chamber of the subject's heart. In such case, the plurality of complex level parameters within the bipolar activity window that are determined may be selected from a group consisting of: complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV). An atrial cardiac arrhythmia site for treatment by ablation may then be determined as an atrial tissue site that includes respective locations corresponding to at least three unipolar ECGs that include at least three successive of FUESCs.

The method may be performed where the plurality of complex level ratings are calculated using parameters selected from a group consisting of: number of slopes (CN), maximum amplitude (CA), maximum slope (CV), relative amplitude range (AREST), relative slope range (VREST), absolute amplitude range (ASCALE), and absolute slope range (VSCALE) and where the QoA is calculated based on at least two parameters of the group consisting of: ASCALE, VSCALE, AREST, VREST, CAR, CVR, unipolar/bipolar slope overlap (UBO), CMS, CTS, and CDE.

The method may further determine a potential type of the complexes of the first unipolar electrogram as either a single potential, a double potential, a fractionated potential or a highly fractionated potential and then calculate the QoA with respect to the complexes of the first unipolar ECG based on the formula:

$$QoA = 100 * \left(\sum_{i=1}^{N} P_i * w_{p,i}\right) \Big/ \sum w_{pi}$$

where N is the number of parameters, $P_i$ is the value of the ith of the N parameters listed above, $w_{p,i}$ is a weight value for the ith parameter depending on a potential type p.

The method may also calculate the final score with respect to the complexes of the first unipolar ECG as a percentage of the sum of EVI plus M, where EVI is determined as a percentage based on a table entry corresponding to an amplitude scale, complex width, and amplitude ratio classification and a number of slopes and the potential type of the first unipolar ECG and M is calculated as a percentage value based on the formula:

$$M = \left[2 * \left(1 - \frac{EVI}{100}\right) * QoA\right] + (EVI - 100).$$

A tangible non-transitory computer-readable medium can be provided to perform the FUESC identification. An example tangible non-transitory computer-readable medium in which program instructions are stored, which, when read by a processor, can cause the processor to:

- process electrocardiogram (ECG) signals in the form of bipolar and unipolar ECGs associated with respective cardiac tissue locations based on sensing locations of respective distal end sensors of a catheter,
- identify Fractionated Unipolar ECG Signal Complexes (FUESCs) from among the recorded unipolar ECGs with respect to unipolar ECGs of a cardiac tissue area of study that include signals from a plurality of successive heartbeats corresponding to locations within the cardiac tissue area of study, where the FUESCs identification is by:
  - determining bipolar activity windows from a bipolar ECG comprising a first unipolar ECG and a second unipolar ECG and defining a series of complexes of the first unipolar ECG that each correspond to a respective bipolar activity window;
  - determining a plurality of complex level parameters with respect to the complexes of the first unipolar ECG with respect to a plurality of successive bipolar activity windows;
  - calculating a plurality of complex level ratings based on at least one of the plurality of complex level parameters;
  - calculating a quality of annotation measurement (QoA) with respect to the complexes of the first unipolar ECG using a plurality of parameters that include at least one of the plurality of complex level parameters and at least one of the plurality of complex level ratings;
  - determining an evidence annotation measurement (EVI) with respect to the complexes of the first unipolar ECG using at least one of the plurality of complex level parameters and at least one of the plurality of complex level ratings; and
  - calculating a final score with respect to the complexes of the first unipolar ECG based on the QoA and the EVI of each complex such that a complex of the first unipolar ECG is determined to be a FUESC upon a condition that its final score is at least a predetermined threshold; and
- determine a cardiac arrhythmia site for treatment by ablation as a cardiac tissue site that includes respective locations corresponding to a predetermined number of unipolar ECGs that include a predetermined number of FUESCs.

The tangible non-transitory computer-readable medium may specifically cause the processor to:

- identify FUESCs from among the recorded unipolar ECGs with respect to unipolar ECGs that include signals from at least ten successive heartbeats and a cardiac tissue area of study that is atrial tissue of at least a portion of an atrial chamber of the subject's heart;
- determine the plurality of complex level parameters within the bipolar activity window selected from a group consisting of: complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV);
- calculate the plurality of complex level ratings using parameters selected from a group consisting of: number of slopes (CN), maximum amplitude (CA), maximum slope (CV), relative amplitude range (AREST), relative slope range (VREST), absolute amplitude range (ASCALE), and absolute slope range (VSCALE);

calculate the QoA based on at least two parameters of the group consisting of: ASCALE, VSCALE, AREST, VREST, CAR, CVR, unipolar/bipolar slope overlap (UBO), CMS, CTS, and CDE;

determine a potential type of the complexes of the first unipolar electrogram as either a single potential, a double potential, a fractionated potential or a highly fractionated potential; and determine an atrial cardiac arrhythmia site for treatment by ablation is determined as an atrial tissue site that includes respective locations corresponding to at least three unipolar ECGs that include at least three successive of FUESCs.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
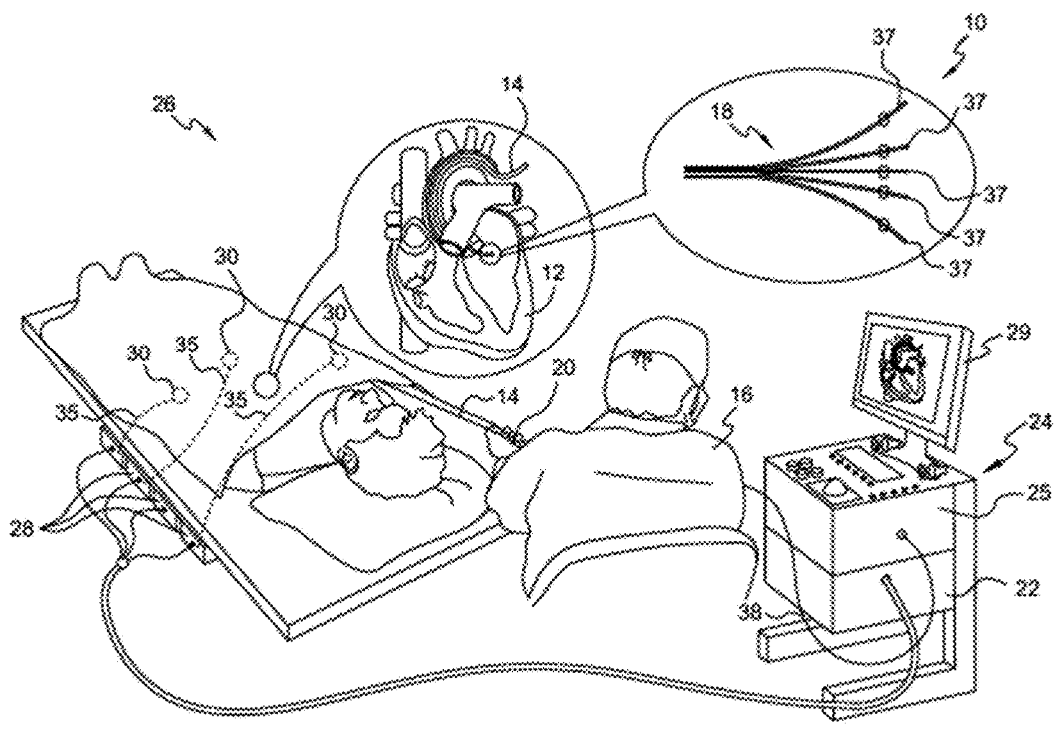
FIG. 1 is a schematic, pictorial illustration of an apparatus for performing procedures on a heart of a living subject using a cardiac catheter having multiple branches, according to an exemplary embodiment.

FIG. 1 is a schematic, pictorial illustration of an example medical apparatus 10 for performing procedures on a heart 12 of a living subject, according to an embodiment. The apparatus 10 includes one or more catheters such as a catheter 14 and a control console 24.

The catheter 14 may be used for any suitable therapeutic and/or diagnostic purposes, such as anatomical mapping of a cavity in a heart 12 of a subject. The catheter 14 may be a multi-electrode catheter having an elongated body with multiple branches 37, each having mapping and location sensing capabilities. The catheter 14 may further comprise a handle 20, having controls which enable an operator 16, who is typically a physician, to steer, position and orient the distal end 18 of the catheter 14 and the location and orientation of the branches 37 as necessary. The catheter described in U.S. Pat. No. 6,961,602, having five branches, is suitable for use as the catheter 14. This catheter is available as the Pentaray™ catheter or probe from Biosense Webster.

In some embodiments, the example catheter 14 comprises an elongated body having a proximal end, a distal end 18, and at least one lumen extending longitudinally therethrough, and a mapping assembly mounted at the distal end of the catheter body and comprising at least two branches 37. Each branch 37 has a proximal end attached at the distal end of the catheter body and a free distal end. Each branch 37 comprises a support arm having shape memory, a non-conductive covering in surrounding relation to the support arm, at least one location sensor 41 (FIG. 2) mounted in the distal end of the branch 37, one or more electrodes mounted on the distal end of the branch 37 and electrically isolated from the support arm, and one or more electrode lead wires extending within the non-conductive covering, each electrode wire being attached to a corresponding electrode. In some embodiments, additional location sensors (not shown) may be disposed on the shaft of the catheter 14 proximal to the branches 37.

The catheter 14 may be percutaneously inserted by the operator 16 through the patient's vascular system into a chamber or vascular structure of the heart 12. The operator 16 may bring the catheter's distal tip 18 in contact with the heart wall at a desired mapping site. The distal end 18 of the catheter 14 may then collect measurements which are stored and processed by a computer or other computing device 22 that comprises a processor and associated data storage memory. The collected measurements may be referred as "points." Each point comprises a three-dimensional coordinate on the tissue of cavity and a respective measurement of some physiological property that is measured at this coordinate. The sensing data may also take the form of unipolar or bipolar electrocardiograms (ECGs) that include signals from a plurality of successive heartbeats corresponding to locations within a cardiac tissue area of study. The data storage of the computing device may include and or be associated with a remote recording device (not shown).

Additionally, or alternatively, ablation energy and electrical signals may be conveyed to and from the heart 12 through one or more optional ablation electrodes located at or near the distal tip 18 through a cable to the console 24. Pacing signals and other control signals may be conveyed from the console 24 through the cable 38 and the one or more ablation electrodes to the heart 12.

Wire connections 35 may link the console 24 with body surface electrodes 30 and other components of a positioning sub-system. A temperature sensor 43 (FIG. 2), such as a thermocouple or thermistor, may be mounted on or near the distal tip 18.

The console 24 may comprise one or more ablation power generators 25. The catheter 14 may be adapted to conduct ablative energy to the heart using any known ablation technique, including but not limited to, radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The computing device 22 may be an element of a positioning system 26 of the apparatus 10 that measures location and orientation coordinates of the catheter 14.

In some embodiments, the positioning system 26 may comprise a magnetic position tracking arrangement that determines the position and orientation of the catheter 14 by generating magnetic fields in a predefined working volume in its vicinity and sensing these fields at the catheter using field generating coils 28 and may include impedance measurements, as taught, for example in U.S. Pat. No. 7,756,576, which is herein incorporated by reference. The positioning system 26 may be enhanced by position measurements using the impedance measurements described in U.S. Pat. No. 7,536,218, which is herein incorporated by reference.

As noted above, the catheter 14 is coupled to the console 24, which enables the operator 16 to observe and regulate the functions of the catheter 14. Console 24 includes the computing device 22. The computing device 22 may be coupled to a display 29. In some embodiments, the display 29 may comprise a graphical user interface (GUI) 29. The signal processing circuits may receive, amplify, filter, and digitize signals from the catheter 14, including signals generated by the above-noted sensors and a plurality of location sensing electrodes (not shown) located on the catheter 14. The digitized signals may be received and used by the console 24 and the positioning system 26 to compute the position and orientation of the catheter 14 and to analyze the electrical signals from the electrodes.

Figure 3:
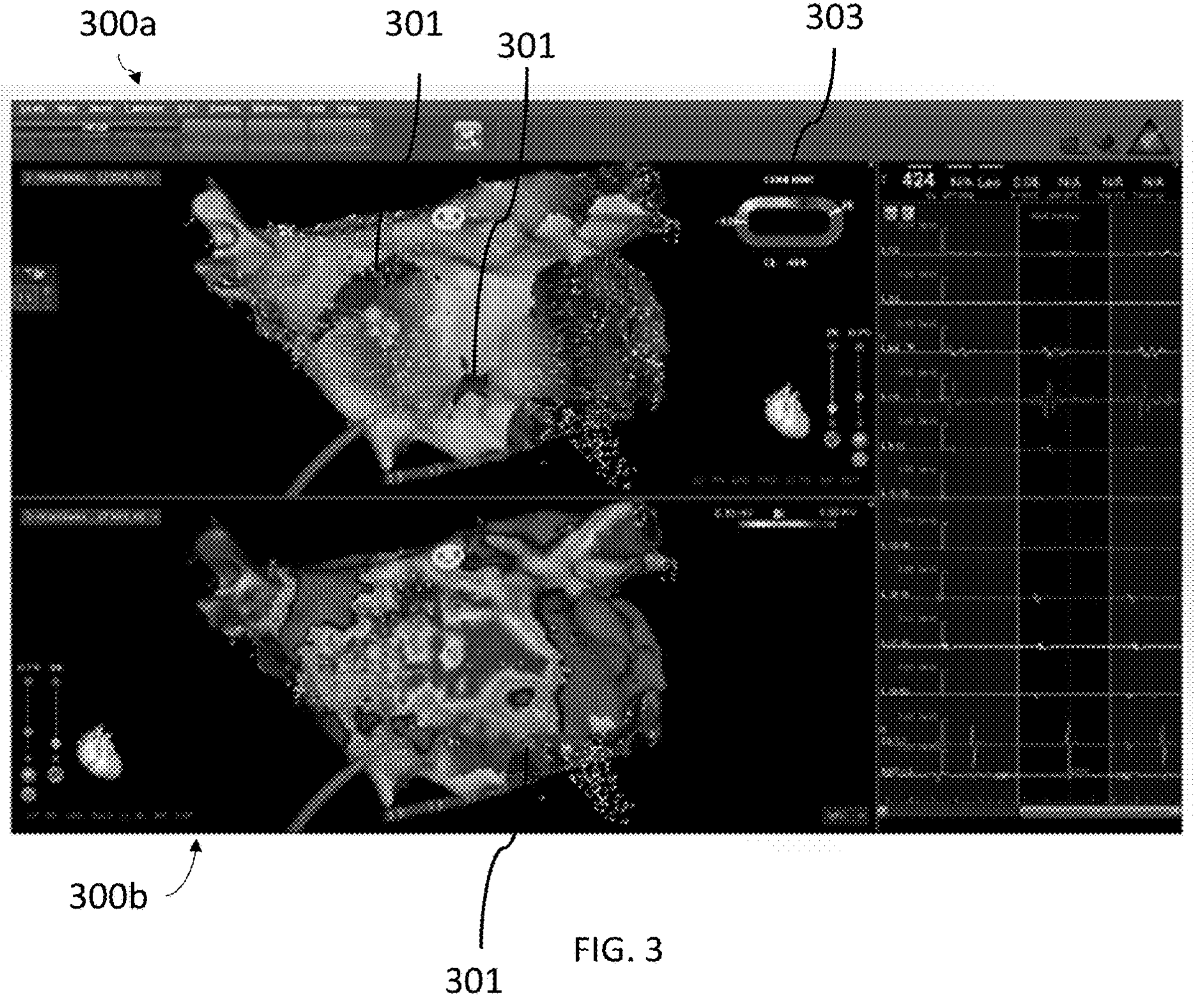
FIG. 3 is an example of a three-dimensional cardiac mapping.

The example computing device 22 is preferably configured to output selected desired visualizations of the subject's heart 12 are output to the display with the relative location of the distal ends of one or more catheters being deployed therein as well as color representation of various characteristics of heart tissue that enable the physician to see characteristic differences in different portions of a heart tissue. Such visualizations' may be accompanied by graphic representations of electrocardiogram (ECG) signals or the like such as illustrated in FIG. 3 (color omitted).

In some embodiments, the computing device 22 may be a computer, and may be programmed in software to carry out the functions described herein. For example, in some embodiments, the computing device 22 is a programmed digital computing device comprising a central processing unit (CPU), a graphics processing unit (GPU), a random-access memory (RAM), non-volatile secondary storage, such as a hard drive or CD ROM drive, network interfaces, and/or peripheral devices. Program code, including software programs, and/or data are loaded into the RAM for execution and processing by the CPU and/or GPU, and results are generated for display, output, transmittal, or storage, as is known in the art. The software code may be downloaded to the computer in electronic form over a network, or it may be provided and/or stored on non-transitory tangible media, such as magnetic, optical or electronic memory.

One commercial product embodying a number of elements of such an apparatus 10 is available as the CARTO® 3 System, available from Biosense Webster, Inc., 3333 Diamond Canyon Road, Diamond Bar, California 91765. Existing such systems provide physicians with selective three-dimensional visualizations of a subject's heart with the relative location of the distal ends of one or more catheters being deployed therein as well as color representation of various characteristics of heart tissue. Examples of such mappings performed with a CARTO® 3 System are illustrated and discussed in *Three-Dimensional Mapping of Cardiac Arrhythmias—What Do the Colors Really Mean?*, Munoz et al., *Circulation: Arrhythmia and Electrophysiology*, 2010, Volume 3, Issue 6: e6-e11, originally published Dec. 1, 2010, https://doi.org/10.1161/CIRCEP.110.960161, which publication is incorporated herein by reference as if fully set forth.

Figure 2:
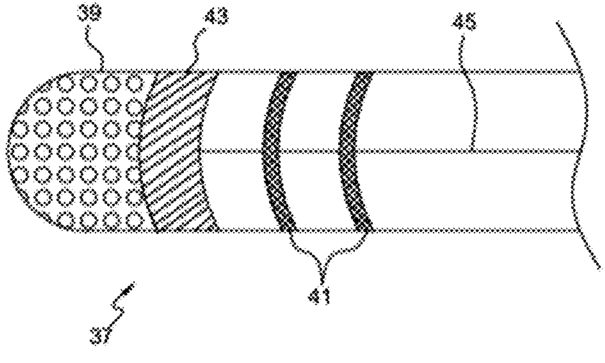
FIG. 2 is a is a detailed view of one of the branches of the catheter shown in FIG. 1, according to an exemplary embodiment.

FIG. 2 is a detailed view of one of the branches 37 of the distal end 18 of the example catheter 14 shown in FIG. 1, illustrating an electrode configuration, according to an embodiment. This example electrode configuration comprises a tip electrode 39, two ring electrodes 41, and a temperature sensor 43. The tip electrode 39 may be configured for both sensing and ablation. The temperature sensor 43 may be used when the catheter 14 is in an ablation mode. The two ring electrodes 41 may be configured as sensing electrodes to detect electrophysiologic signals in the heart. However, as will be appreciated by one having ordinary skill in the art, the sensing electrodes and ablation electrodes may vary in number, configuration, and distribution in many combinations. One or more cables 45 may communicate signals between the electrodes, sensors, and the console 24. With multiple electrodes distributed in several branches 37, it is possible to collect signals from many locations simultaneously.

In current systems, a catheter, such as the catheter 14 described above, is moved within a chamber of a heart or within an adjoining blood vessel and the location of the catheter 14 is continually recorded. The computing device 22 may receive the respective coordinates of a plurality of locations within the chamber of the heart. For example, as described above with respect to FIG. 1, a CPU may receive coordinates from a location-ascertaining routine, which ascertains the location of the distal end of the catheter 14 as the distal end is moved within the chamber. Each coordinate may be referred to as a "point" and the collection of coordinates may be referred to as a "point cloud." The point cloud may include hundreds, thousands, or tens of thousands of points, along with gaps in which no points are present.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

FIG. 3 is a first view of a three-dimensional cardiac mapping 300*a* and a second view of a three-dimensional cardiac mapping 300*b*, according to an embodiment (color omitted). The three-dimensional cardiac mapping 300*a*, 300*b* comprises low voltage regions 301, which are shaded. In the colorization of the cardiac mappings, different colors may be used to indicate different degrees of voltage with respect to the displayed cardiac image and a gradient scale 303 may be displayed for the operator's convenience. In one example of an atrial chamber mapping, regions having a voltage measurement of 0.1 mV or less are displayed with a red color indicating a low voltage region and regions having a voltage measurement of 0.5 mV or more are displayed with a pink color indicating a high voltage region with regions having voltage between the low and high voltage thresholds displayed with a color on the gradient scale corresponding to that voltage.

Typically, low voltage regions of a cardiac mapping are associated with diseased or affected tissue. Currently, an operator, such as a physician, lacks the ability to accurately evaluate such low voltage regions. Often, the operator does not know what is happening in a low voltage region. It would be advantageous to identify fractionation signals within low voltage regions to determine what is occurring in the region and whether ablation should be performed at the region.

Systems, devices and methods for faster and more reliable identification of target ablation sites by automatic identification of fractionated signals that are, for example, related to low voltage sites are disclosed. As explained in detail below, unipolar electrograms of unipolar electrode pairs associated with selected cardiac tissue areas are analyzed scored to determine if they represent fractionated signals. The selected area of study may, for example, be an entire atrial chamber or an area encompassing a low voltage region within an atrial chamber.

Figure 4:
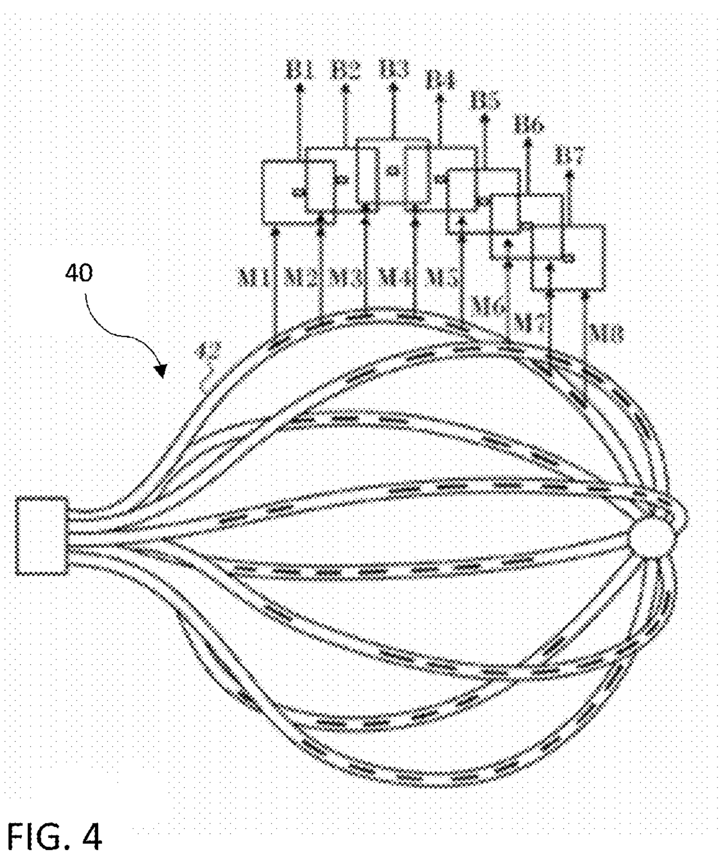
FIG. 4 is a diagram of an example basket cardiac chamber mapping catheter.

Reference is now made to FIG. 4, which is a diagram of a basket cardiac chamber mapping catheter 40, according to an embodiment. The basket cardiac chamber mapping catheter 40 may be used as catheter 14 described above. Catheter 40 is similar in design to the basket catheter described in U.S. Pat. No. 6,748,255, to Fuimaono, et al., which is assigned to the assignees of the present invention and herein incorporated by reference. The catheter 40 has multiple ribs, each rib having at multiple electrodes. In one embodiment the catheter 40 has 64 unipolar electrodes, and may be configured with up to 7 bipolar pairs per rib. For example, rib 42 has unipolar electrodes M1-M8, with bipolar configurations B1-B7. In this example, the inter-electrode distance may be 4 mm.

Figure 5:
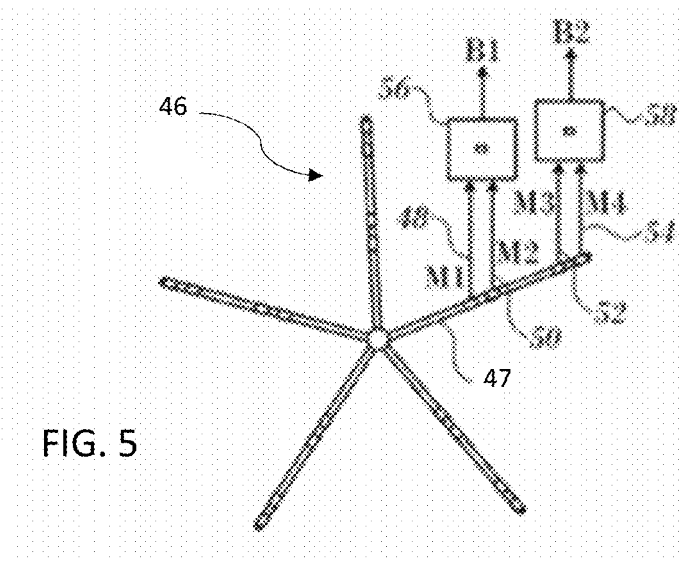
FIG. 5 is a diagram of an example spline catheter.

Reference is now made to FIG. 5, which is a diagram of an example of a spline catheter 46 that may be used as catheter 14 described above. The catheter 46 has multiple distal end branches, each branch having several electrodes. The example catheter 14 of FIG. 4 has 20 unipolar electrodes, which may be configured as either two or three bipolar pairs per branch. For example, branch 47 has a first pair of unipolar electrodes 48, 50 and a second pair of unipolar electrodes 52, 54 (M1-M4). Respective differences between the unipolar electrode pairs are calculated in blocks 56, 58. The outputs of blocks 56, 58 (B1, B2) may be associated with one another to constitute a hybrid bipolar electrode configuration, an arrangement referred to herein as a "double bipolar configuration". In this example, the inter-electrode distances may be 4-4-4 or 2-6-6 mm.

Figure 6A:
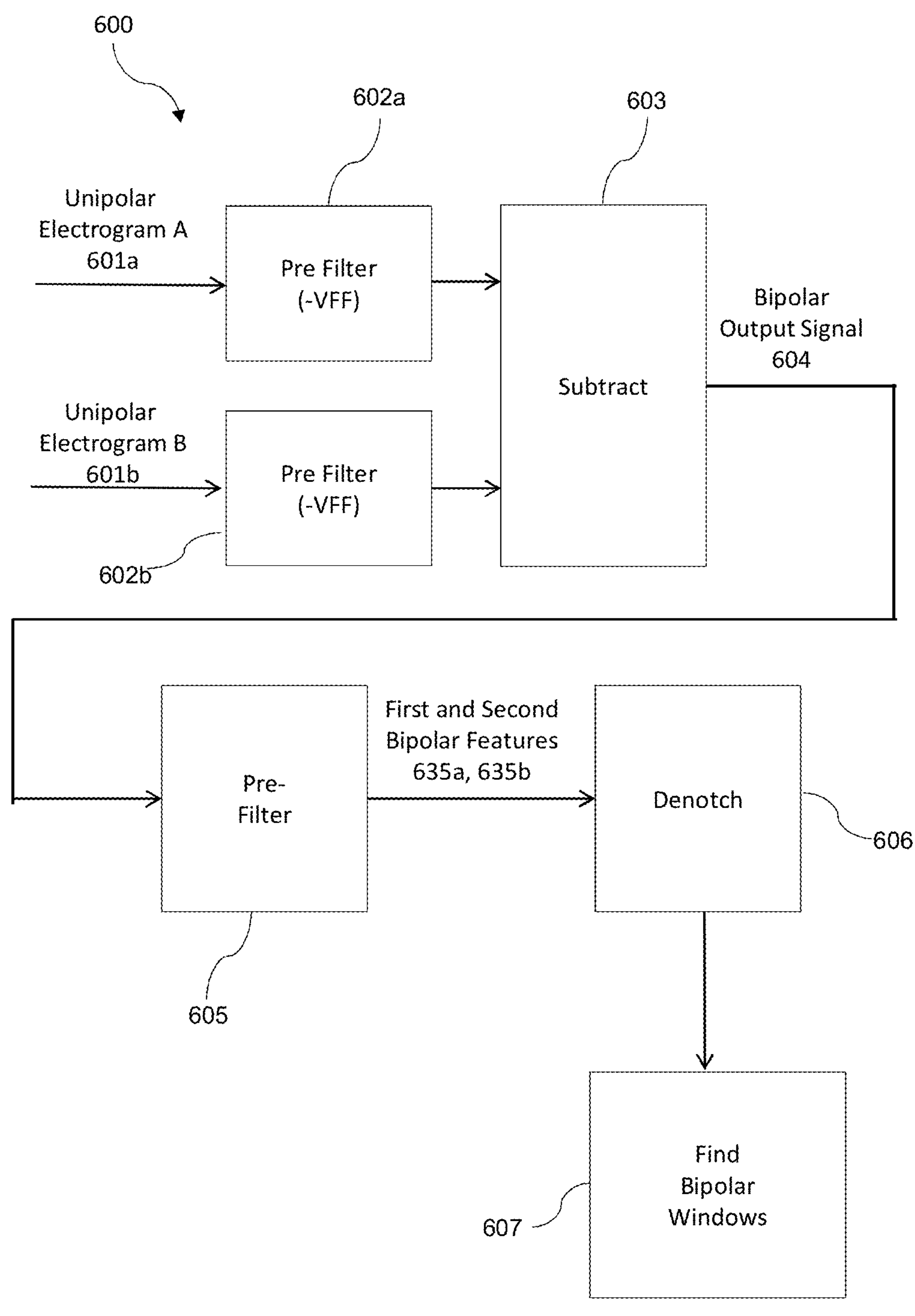
FIG. 6A is a flow diagram of a process for determining a bipolar activity window, according to an exemplary embodiment.

FIG. 6A is a flow diagram illustrating a process for determining a bipolar activity window 600, according to an embodiment. At 602, a pre-filter is applied to two unipolar electrograms 601*a* and 601*b*. The unipolar electrograms 601*a* and 601*b* are typically generated from pairs of neighboring electrodes. In conducting an atrial chamber study, the pre-filter may be configured to remove ventricular far field (VFF) effects. Far field reduction can be accomplished using the teachings of commonly assigned patent application Ser. No. 14/166,982, entitled Hybrid Bipolar/Unipolar Detection of Activation Wavefront, which is herein incorporated by reference.

At 603, the outputs of the pre-filter blocks 602*a* and 602*b* are subtracted in order to determine a bipolar electrogram 604. At 605, one or more pre-filters are applied to the bipolar electrogram 604. At 606, a denotch filter may be applied to the first bipolar feature signal 635*a* and the second bipolar feature signal 635*b*. At 607, time intervals comprising a window-of-interest (hereinafter referred to as "bipolar activity window") may be determined for the first bipolar feature electrogram 635*a* and the second bipolar feature electrogram 635*b*. Different methods may be used to determine the bipolar activity window, as discussed in more detail with respect to FIGS. 7 and 8.

Figure 6B:
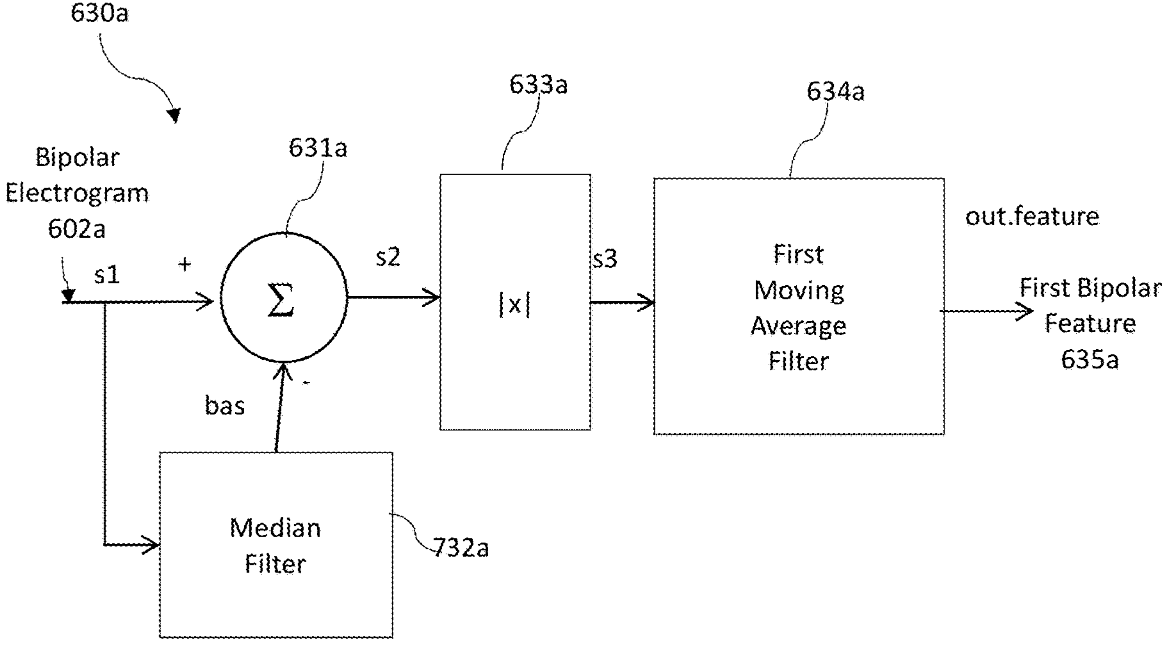
FIG. 6B is a flow diagram of the pre-filter process, according to an exemplary embodiment.
Figure 6B:
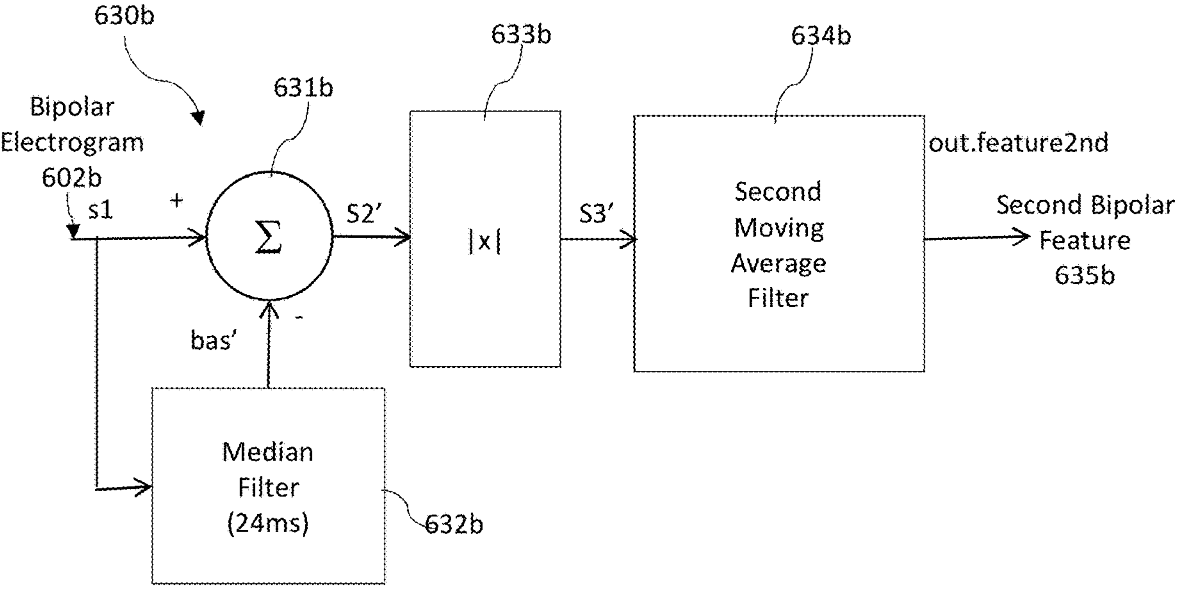

FIG. 6B illustrates flow diagrams 630*a* and 630*b* of the pre-filter process 605, according to an embodiment. At 631*a*, 631*b* a sum may be calculated. At 632*a*, 632*b* a median filter may be applied to the bipolar electrogram 602*a*. A median filtered signal may be determined and used to correct the electrogram signals such that baseline activities are removed from the electrogram signals. At 633*a*, 633*b* the outputs of 621*a*, 631*b* are converted to absolute value. At 634*a*, a first moving average filter may be applied to the output of 631*a*. The moving average filter may take a certain number of samples of input at a time and take the average of those to produce a smoothed output signal referred to as a feature signal. As the length of the filter increases, the smoothness of the output signal increases, whereas the sharp modulations in the data are made increasingly blunt.

At 634*b*, a second moving average filter may be applied to the output of 633*b*. In some embodiments, the first moving average filter may be 40 ms and the second moving average filter may be 10 ms. The output of process 630*a* may be a first bipolar feature 635*a* and the output of process 630*b* may be a second bipolar feature 635*b*.

Figure 6C:
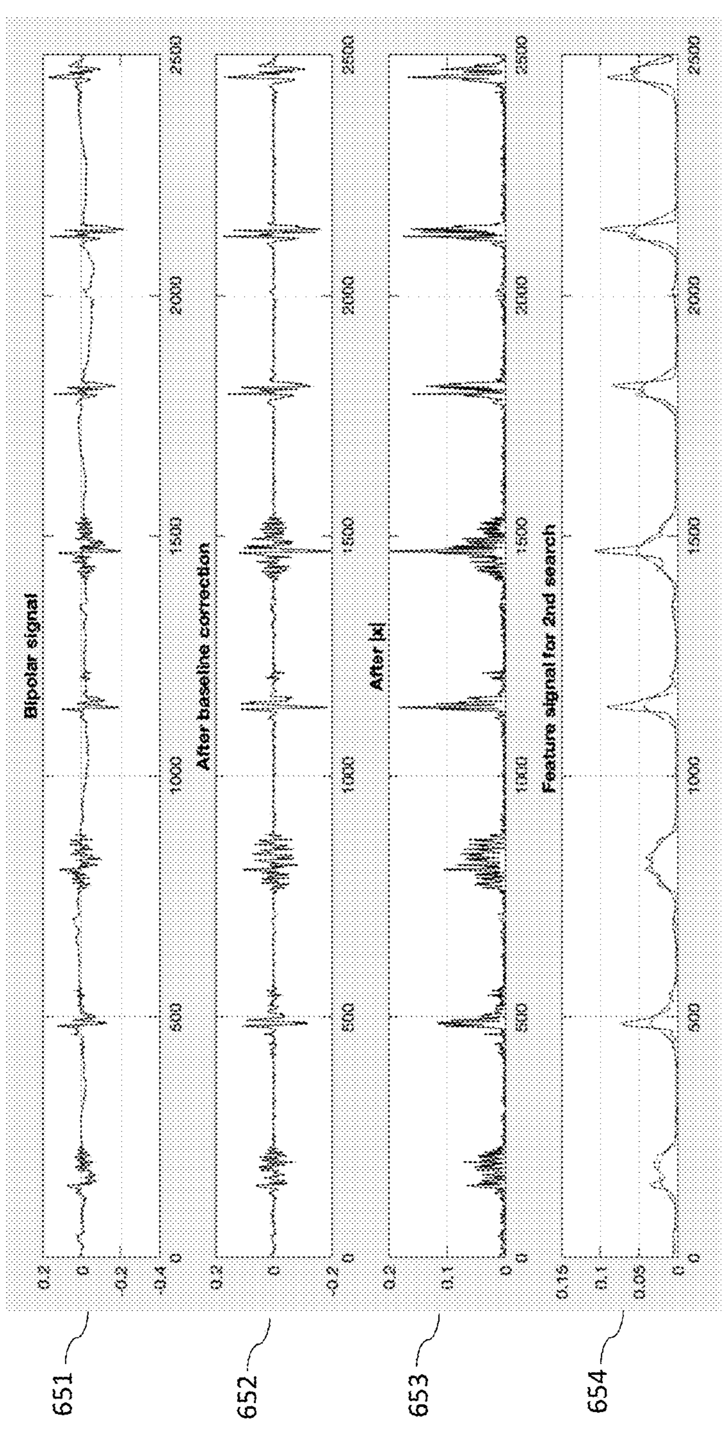
FIG. 6C illustrates an example of a bipolar electrogram during the pre-filter process described in FIG. 6B.

FIG. 6C illustrates an example of bipolar electrograms during the pre-filtering process described in FIG. 6B. Graph 651 illustrates the measured bipolar electrogram. Graph 652 illustrates the bipolar electrogram after the baseline correction using the median (632*a*, 632*b* in FIG. 6B). Graph 653 illustrates the bipolar electrogram after it has been converted to absolute value (633*a*, 633*b* in FIG. 6B). Graph 654 illustrates the resulting first bipolar feature 635*a* and second bipolar feature 635*b* after the moving average filter has been applied (634*a*, 634*b* in FIG. 6B).

Figure 6D:
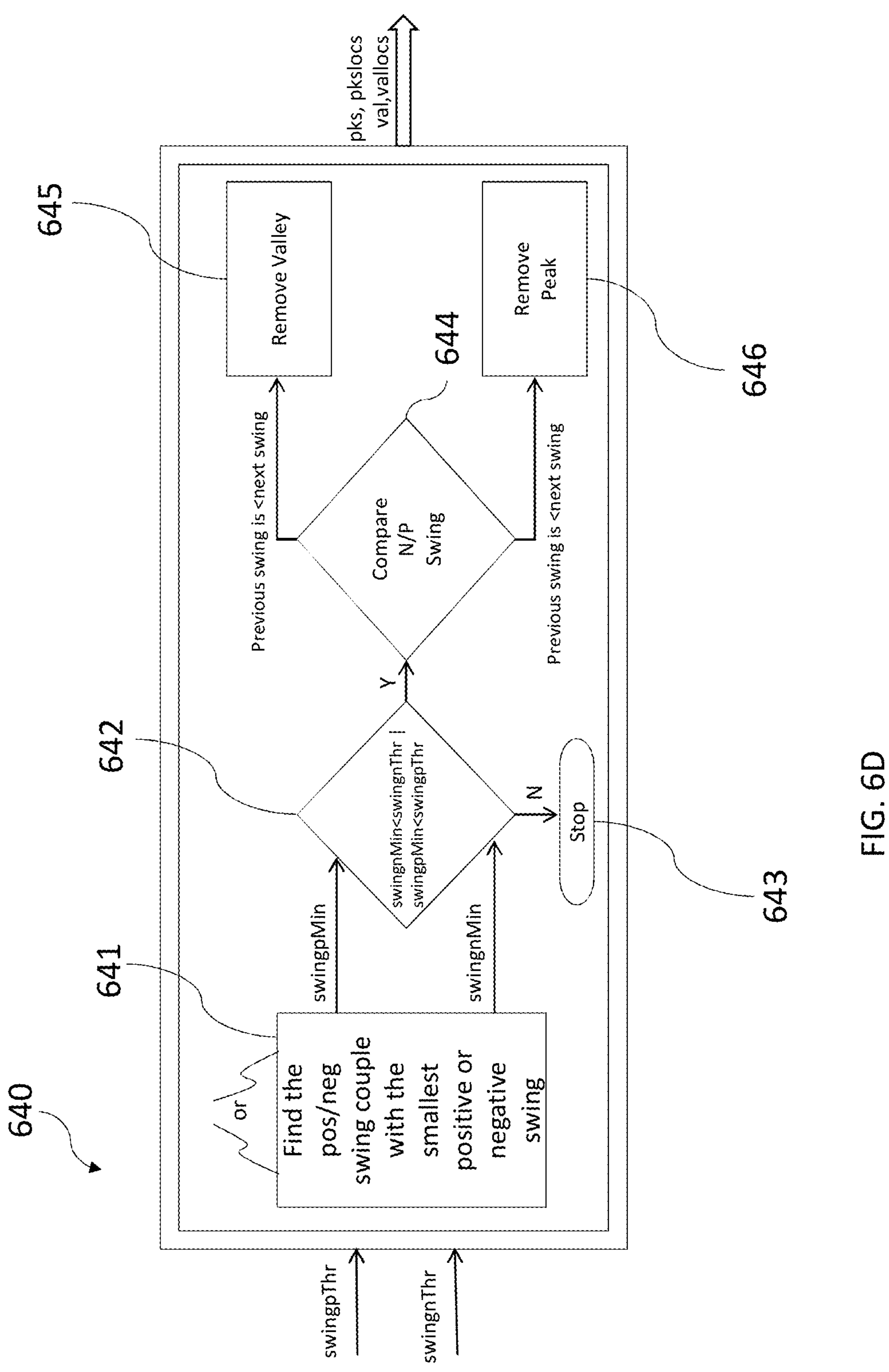
FIG. 6D is a flowchart illustrating the denotch filter, according to an exemplary embodiment.

FIG. 6D is a flowchart of a denotch filter 640, according to an embodiment, that be used at 606 of FIG. 6A. At 641, the positive/negative swing couple with the smallest positive swing (swingpMin) or negative swing (swingpMin) is determined. At 642, if swingpMin is less than a predetermined threshold (swingnThr) or if swingnMin is less than a predetermined threshold (swingnThr), then the process moves to 643. If swingpMin is greater than or equal to swingnThr or if swingnMin is greater than or equal to swingnThr, then the process moves to 644, where the process ends. At 643, the previous swing is compared to the next swing. If the previous negative swing is less than the next negative swing or if the previous positive swing is less than the next positive swing, then the valley is removed at 645 or the peak is removed at 646, respectively.

Figure 7:
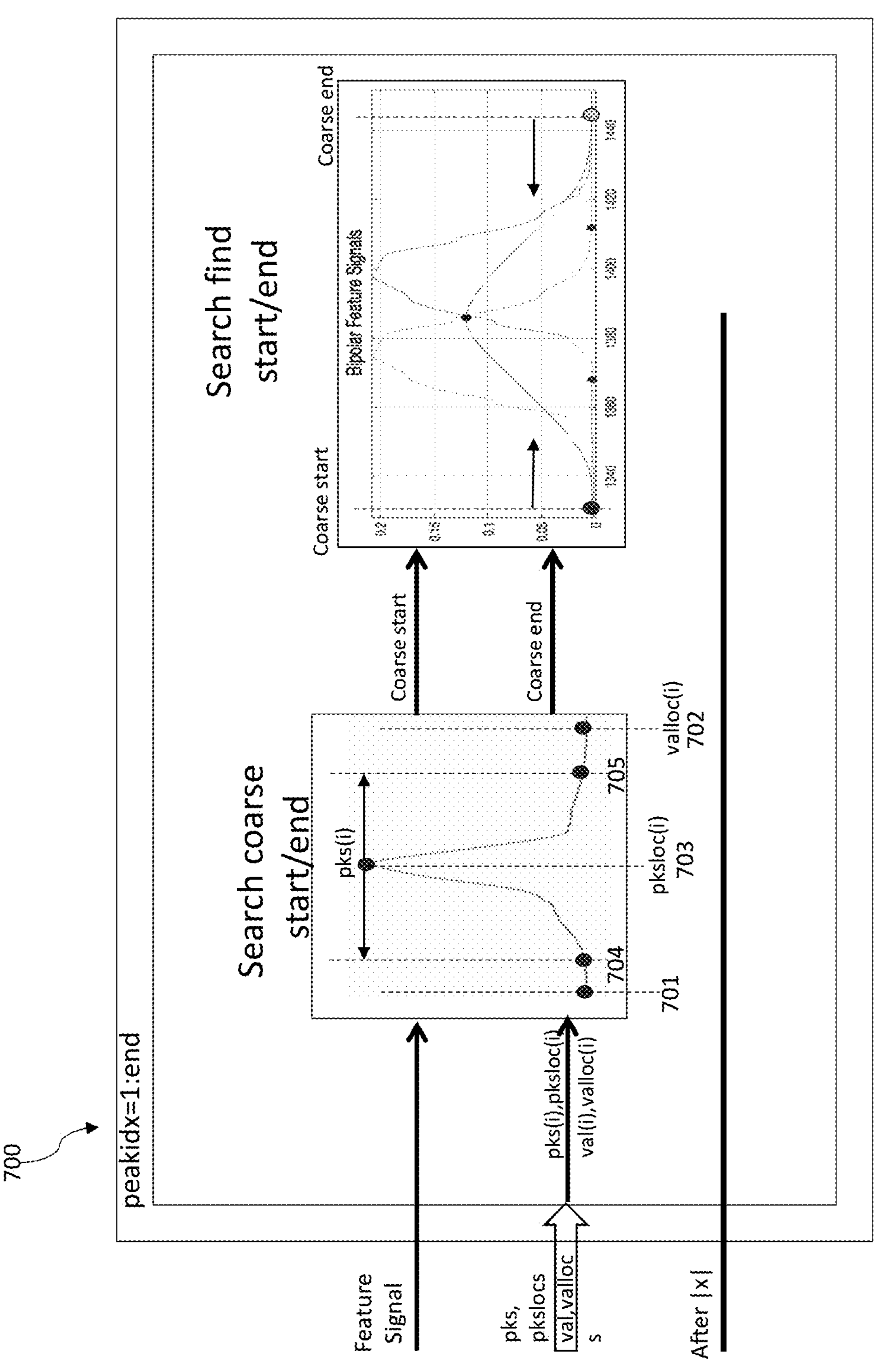
FIG. 7 is a diagram illustrating the process for determining an activity window for a bipolar electrogram, according to an exemplary embodiment.

FIG. 7 is a diagram illustrating an example process for determining an activity window for a bipolar feature 700, according to an embodiment. The process 700 may be used for a bipolar feature signal that is relatively less filtered. For example, the process 700 may be used on the first bipolar feature signal 635*a* for which the moving average filter of 10 ms was applied. Starting at outside points 701 and 702 and moving toward a peak 703, the slope may be calculated to determine if the electrogram is relatively flat (i.e., the slope is under a certain threshold). The respective points indicative of when the electrogram is no longer relatively flat may be determined (points 704 and 705). These points 704 and 705 may be designated as the start and end of the activity window, respectively. The start and end times of the activity window 704, 705 may define a first bipolar feature window.

Figure 8:
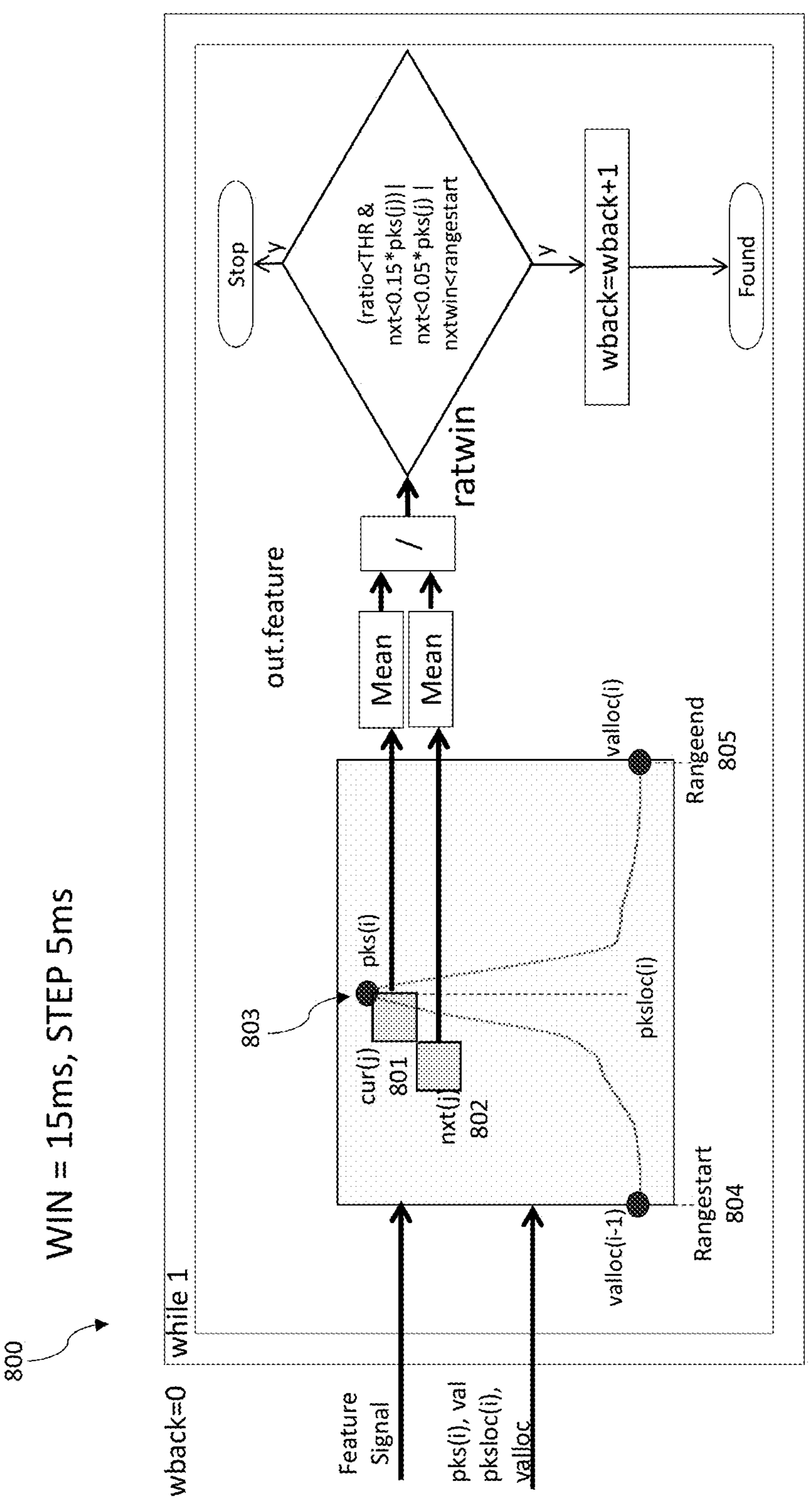
FIG. 8 is a diagram illustrating the process for determining a bipolar activity window, according to an exemplary embodiment.

FIG. 8 is a diagram illustrating an example process for determining an activity window for a bipolar feature 800, according to an embodiment. The process 800 may be used on a bipolar feature that is relatively more filtered. For example, the process 800 may be used on the bipolar feature 635*b* for which the moving average filter of 40 ms was applied. Starting at the peak 803 and moving down, a current mean 801 and a next mean 802 are calculated. If the current mean 801 is greater than the next mean 802, indicating that the electrogram is still descending, then the process continues to move down the electrogram, until the current mean 801 is less than or equal to the next mean 802, shown as points 804 and 805 in diagram 800. Points 804 and 805 may be designated the start and end of the activity window, respectively. The start and end times of the activity window 804, 805 may define a second bipolar feature window.

Figure 9:
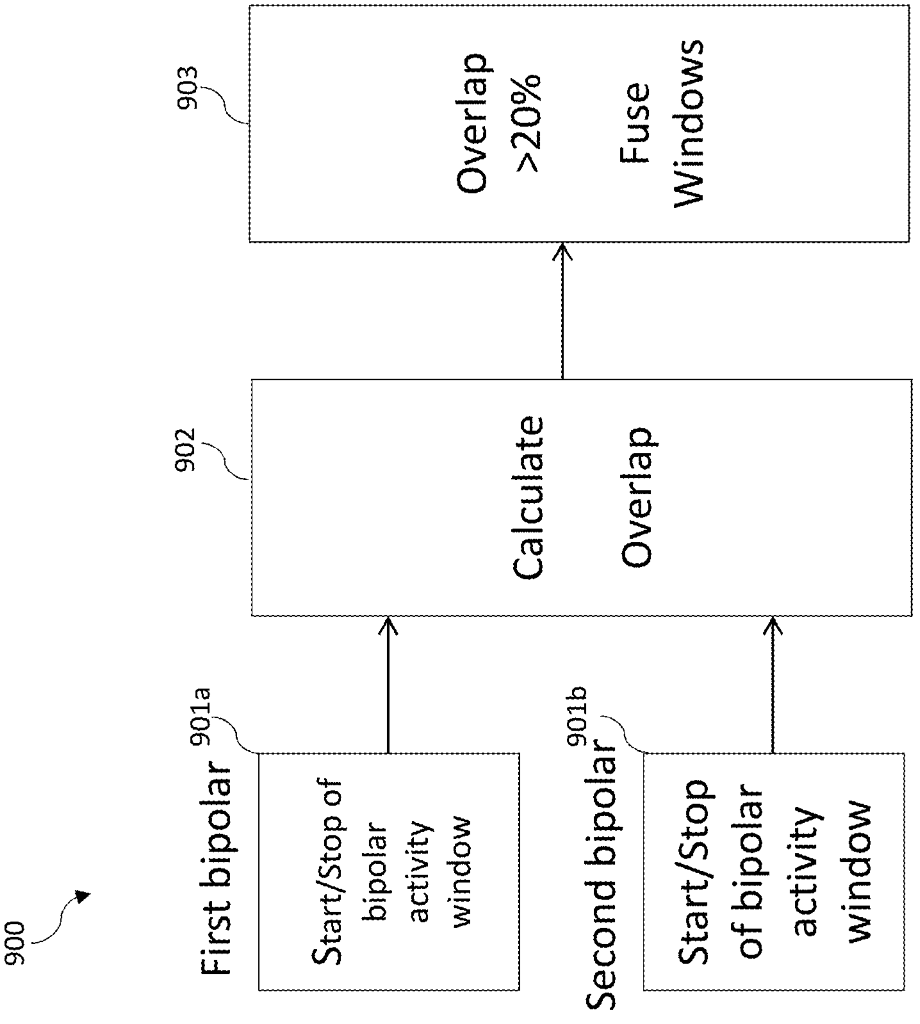
FIG. 9 is a flow diagram illustrating a process for overlapping two bipolar activity windows to determine a bipolar activity window, according to an exemplary embodiment.

FIG. 9 is a flow diagram of fusing previously determined activity windows for bipolar features 900 to determine a bipolar activity window, according to an embodiment. The start and end times of a first bipolar feature window 901*a* (e.g., 704 and 705 of FIG. 7) and the start and end times of the second bipolar feature window 901*b* (e.g., 804 and 805 of FIG. 8) are used to calculate the overlap at 902. Provided the overlap between such windows is 20 percent or greater, the first bipolar feature window 901*a* and the second bipolar feature window 902*b* are fused.

Figure 10:
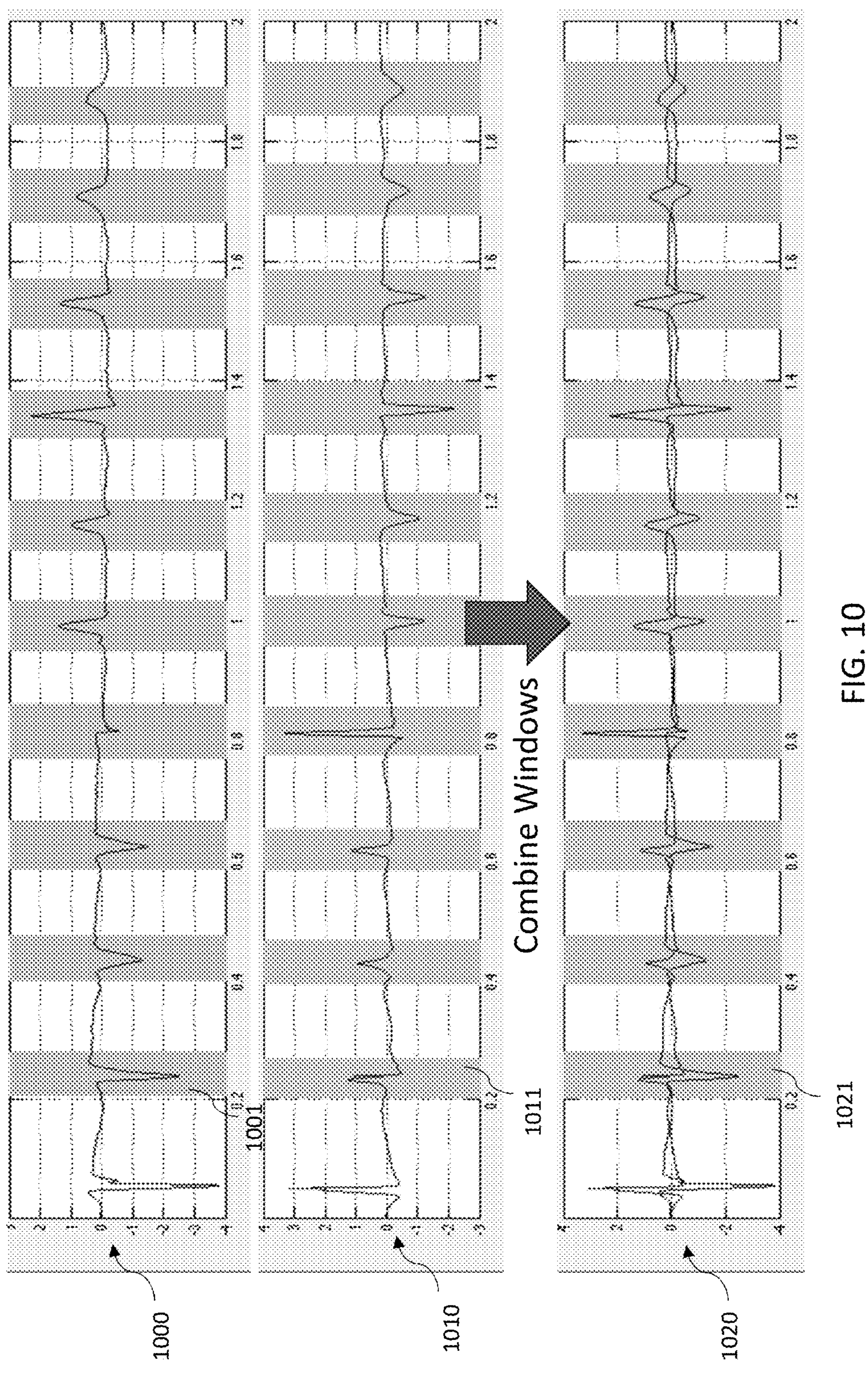
FIG. 10 is an example of a visual representation of the process for overlapping two bipolar activity windows, as discussed with respect to FIG. 9.

FIG. 10 is an example visual representation of the process for overlapping two bipolar activity windows, as discussed with respect to FIG. 9. FIG. 10 comprises a first bipolar feature electrogram 1000 with designated activity windows, a second bipolar feature 1010 with designated activity windows, and a combined electrogram 1020 with fused bipolar activity windows. In the example illustrated in FIG. 10, the first bipolar feature window 1001 of the first electrogram 1000 and the second bipolar feature activity window 1011 of the second electrogram were determined to have an overlap greater than the fuse threshold. As such, the first activity window 1001 and the second activity window 1011 may be combined to create a fused bipolar activity window 1021 in the combined bipolar electrogram 1020.

After a bipolar activity window is defined, a unipolar signal within the window may be analyzed according to the methods described below.

Figure 11:
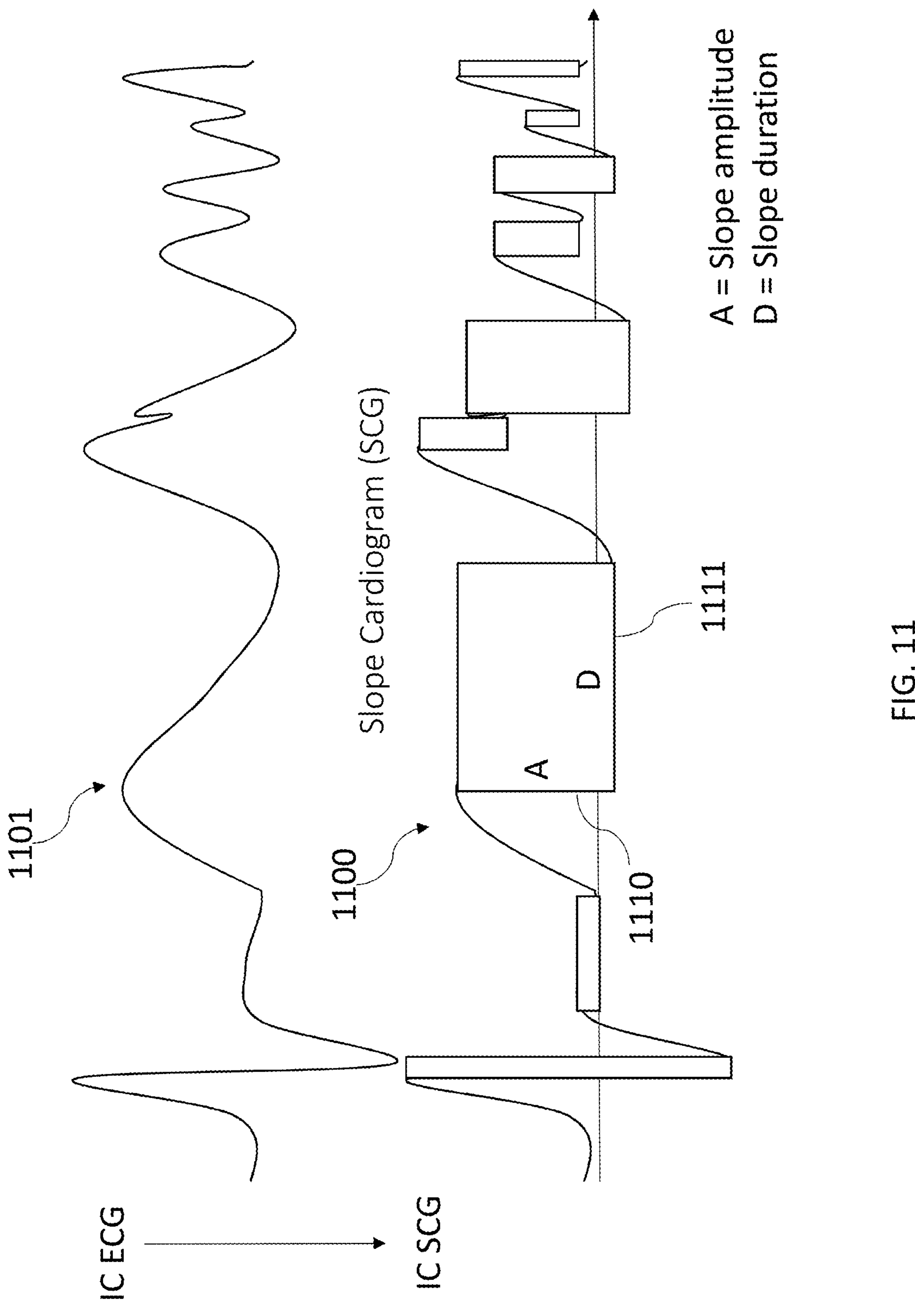
FIG. 11 is a diagram illustrating a slope cardiogram (SCG), according to an exemplary embodiment.

FIG. 11 is a diagram illustrating an example slope cardiogram (SCG) 1100. The corresponding electrogram 1101 is also illustrated. The SCG 1100 shows downward (negative) slope amplitude and duration. In the example illustrated in FIG. 11, the negative slopes are demarcated as rectangles. The width of a rectangle 1110 represents the amplitude of the slope and the length of a rectangle 1111 represents the duration of the slope. The duration and amplitude of a negative slope may be used to determine whether a particular slope is a primary slope, secondary slope, far-field, or noise. Similarly, the slope value and amplitude of a negative slope may be used to determine whether a particular slope is a primary slope, secondary slope, far-field, or noise.

Figures 12A, 12B:
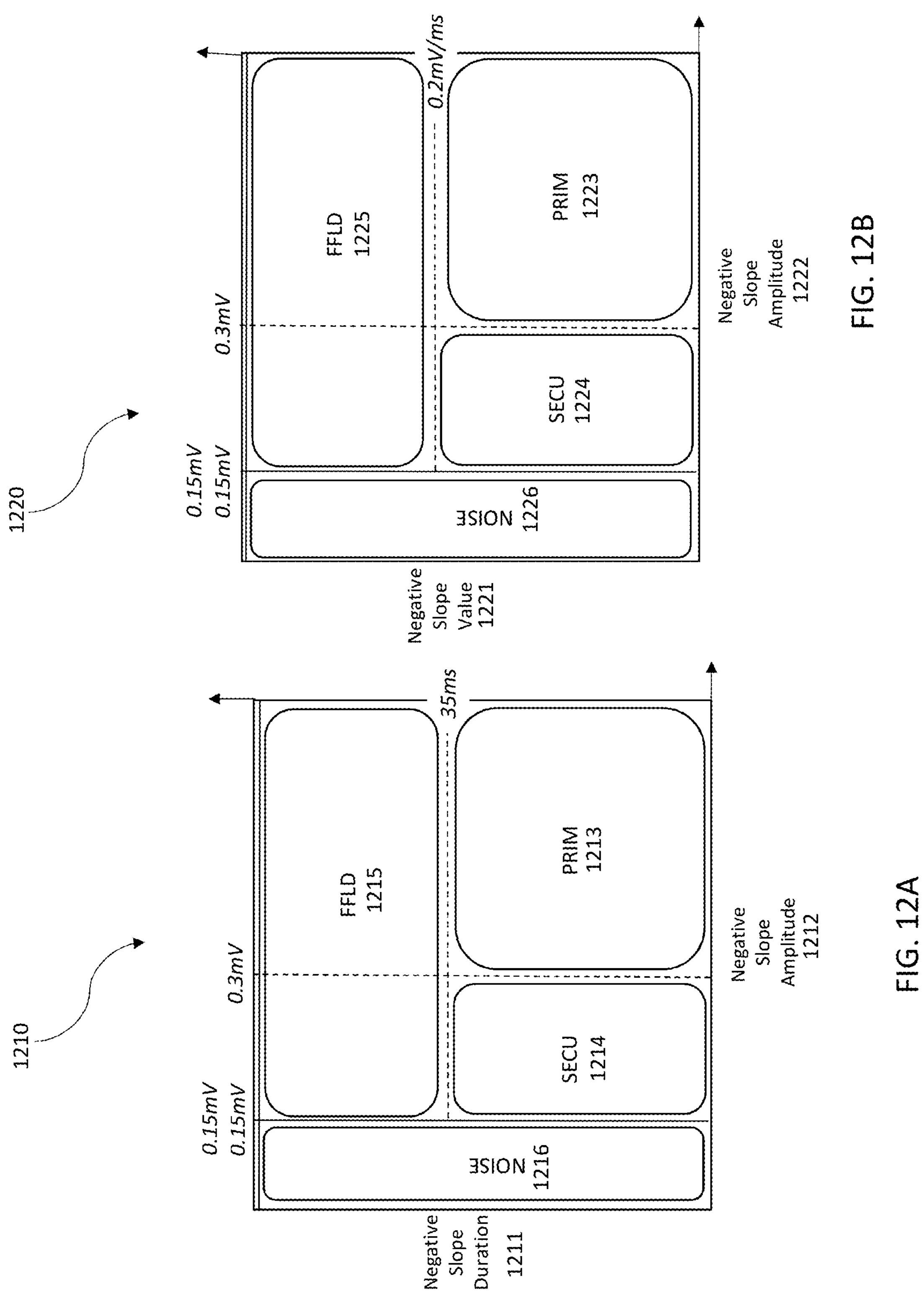
FIG. 12A is a graph of a negative slope's duration vs. the negative slope's amplitude, according to an exemplary embodiment.
FIG. 12B is a graph of a negative slope value vs. the negative slope's amplitude, according to an exemplary embodiment.

FIG. 12A is a graph 1210 of a negative slope's duration 1211 vs. the negative slope's amplitude 1212, according to an embodiment. Depending on where a point representing the negative slope's duration and amplitude falls on the graph, it may be determined whether the negative slope is a primary slope 1213, secondary slope 1214, fair field 1215, or noise 1216. For example, in the embodiment illustrated in FIG. 12A, if a negative slope's amplitude is less than 0.15 mV, then the negative slope is identified as noise, regardless of its duration. If a negative slope's amplitude is greater than 0.3 mV and its duration is greater than 35 ms, the negative slope may be identified as far-field. If a negative slope is identified as either noise or far-field, it may not be counted as a slope in further analyses, discussed in more detail below. If a negative slope's amplitude is greater than 0.3 mV and its duration is less than 35 ms, then it may be identified as a primary slope. If a negative slope amplitude is less than 0.3 mV and its duration is less than 35 ms, then it may be identified as a secondary slope. However, the thresholds provided above are by way of example only, and other thresholds may be utilized.

FIG. 12B is a graph 1220 of a negative slope value 1221 vs. the negative slope's amplitude 1222, according to an embodiment. Depending on where a point representing the negative slope's value and amplitude falls on the graph, it may be determined whether the negative slope is a primary slope 1223, secondary slope 1224, fair field 1225, or noise 1226. For example, in the embodiment illustrated in FIG. 12B, if a negative slope's amplitude is less than 0.15 mV, then the negative slope is identified as noise, regardless of its slope value. If a negative slope's amplitude is greater than 0.15 mV and its slope value is greater than 0.2 mV/ms, the negative slope may be identified as far-field. If a negative slope is identified as either noise or far-field, it may not be counted as a slope in further analyses, discussed in more detail below. If a negative slope's amplitude is greater than 0.3 mV and its slope value is less than 0.2 mV/ms, then it may be identified as a primary slope. If a negative slope amplitude is not more than 0.3 mV. but not less than 0.015 mV, and its slope value is less than 0.2 mV/ms, then it may be identified as a secondary slope. However, the thresholds provided above are by way of example only, and other thresholds may be utilized.

Figure 13:
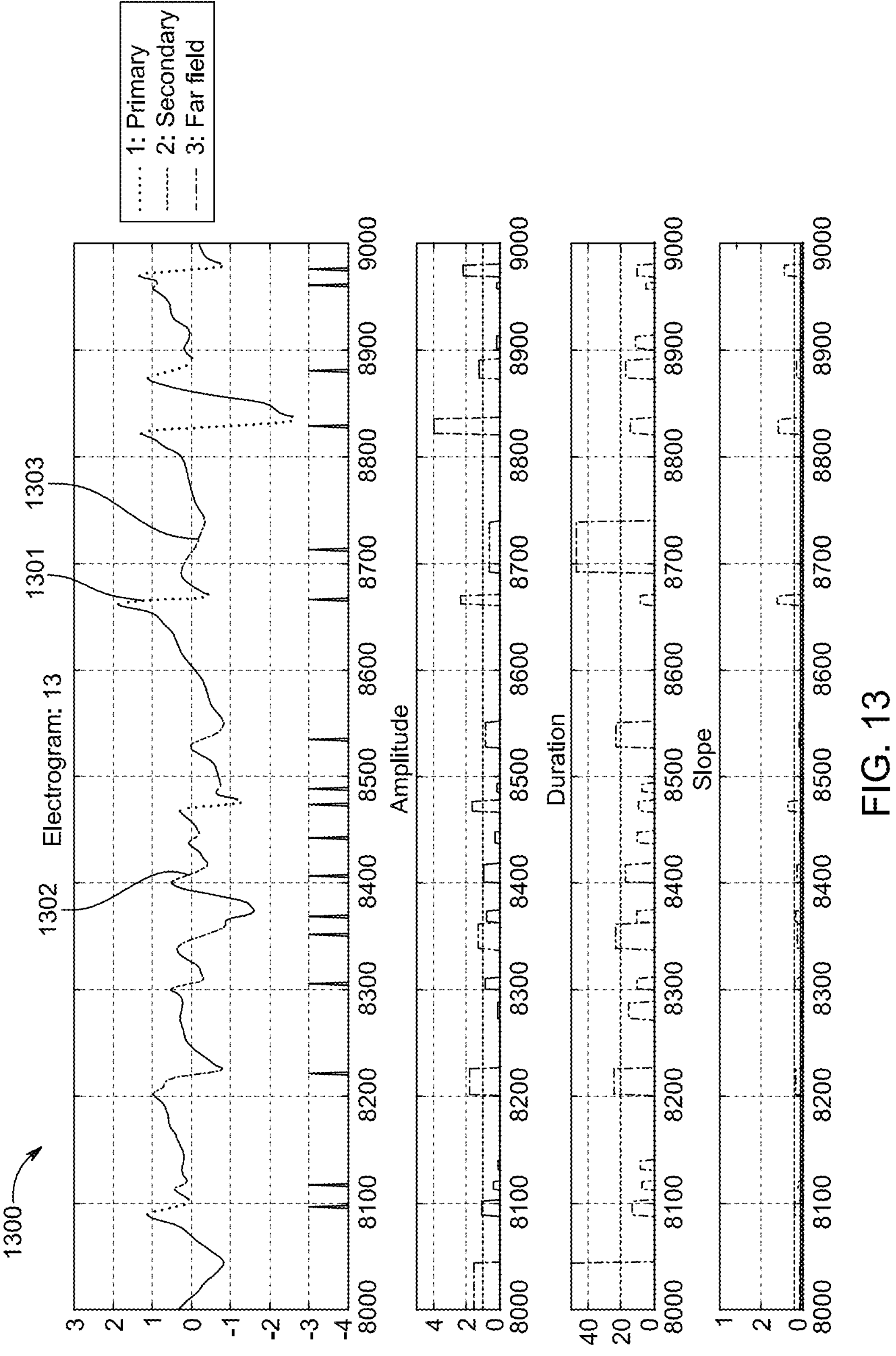
FIG. 13 is an example of a unipolar electrogram with the downward slopes designated as either primary, secondary, or far field.

FIG. 13 is an example unipolar electrogram 1300 with the downward slopes designated as either primary, secondary, or far field. The downward slope type may be determined using the methods described above. The primary downward slopes 1301, the secondary downward slopes 1302, and the far field downward slopes are designated by respective types of broken lines as indicated in the drawing key.

In some embodiments, artifactual slopes may be removed from a unipolar electrogram. In some embodiments, small downward notches related to noise may be removed. Small downward notches related to noise may be defined as slopes with an amplitude of less than 0.02 mV in some embodiments. Additionally, or alternatively, slow downward slopes related to far field potentials may be removed. Slow downward slopes related to far field potentials may be defined as slopes less than 0.03 mV/ms and with a duration greater than 25 ms in some embodiments. Additionally, or alternatively, small upward slopes embedded in large downward slopes may be removed. Upward slopes within large downward slopes with an amplitude of less than 0.05 mV and a duration of less than 5 ms may be defined as small upward slopes embedded in large downward slopes in some embodiments. However, the thresholds provided above are by way of example only, and other thresholds may be utilized.

Significant unipolar slopes within the bipolar activity window may be detected. In some embodiments, downward slopes having a peak or valley within a bipolar activity window qualify for detection. Downward slopes may have to meet certain criteria to be defined as a significant unipolar slope. For example, a significant slope may be defined as a slope with an amplitude of greater than 0.05 mV, a duration of less than 50 ms, a slope of greater than 0.005 mV/ms, and a bipolar activity window with greater than 30% overlap and greater than 100 ms.

Figure 14:
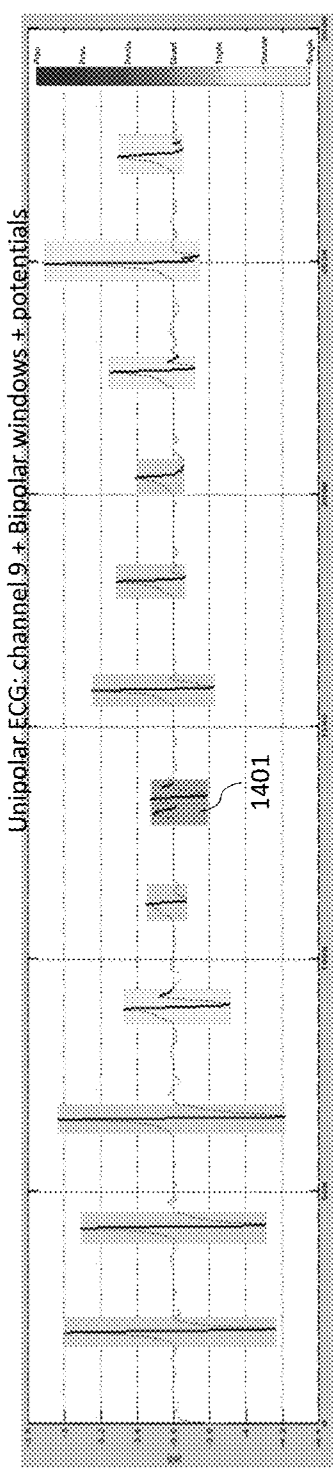
FIG. 14 is an example of a unipolar electrogram with determined bipolar activity windows.

FIG. 14 is an example unipolar electrogram 1400 with determined bipolar activity windows. The number of complexes of unipolar electrogram 1400 within bipolar activity windows, whose amplitude and peak-to-peak intervals meet certain criteria, is determined. In some of the bipolar activity windows, there are multiple activations within a bipolar activity window. In the example illustrated in FIG. 14, the bipolar activity windows are shaded with the amount of shading depending on the number of downward slopes within the window. For example, in FIG. 14, the complex within the bipolar activity window 1401 comprises three slopes. The number of slopes within a bipolar activity window is utilized in the fractionation analysis, as described in more detailed below.

Figure 15:
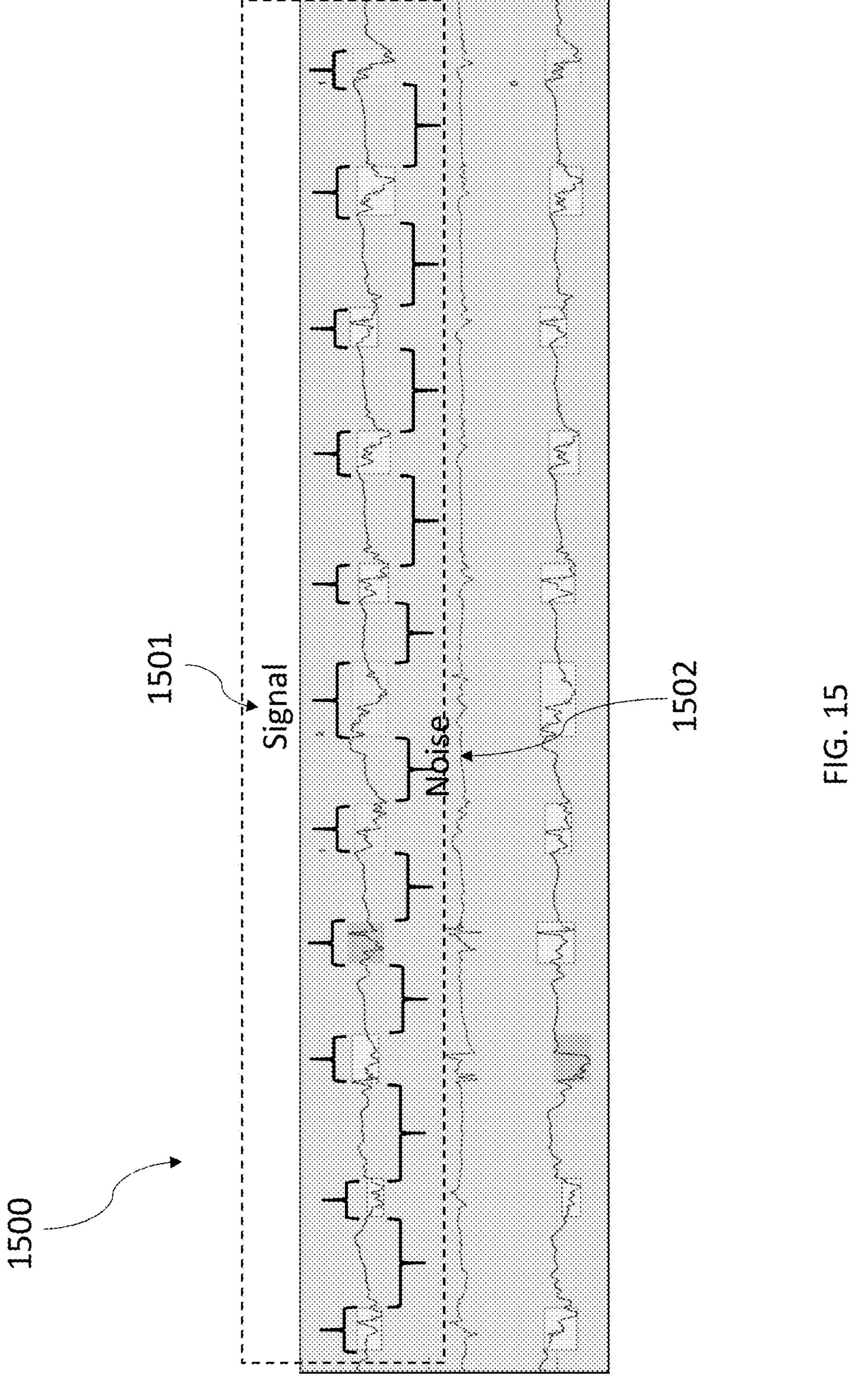
FIG. 15 is an example of a unipolar electrogram illustrating a signal-to-noise-ratio (SNR) calculation.

FIG. 15 is an example unipolar electrogram 1500 illustrating a signal-to-noise-ratio (SNR) calculation. Unipolar complexes 1501 within bipolar activity windows of the unipolar electrogram 1500 are considered signal and portions of the electrogram outside of the bipolar activity window are designated as noise 1502. Root-mean-square (RMS) amplitudes are calculated for respective portions of the electrogram designated as signal and noise. The SNR may then be subsequently calculated as a measure of the signal power. The SNR may be used in the fractionation analysis, as described in more detailed below.

Figure 16:
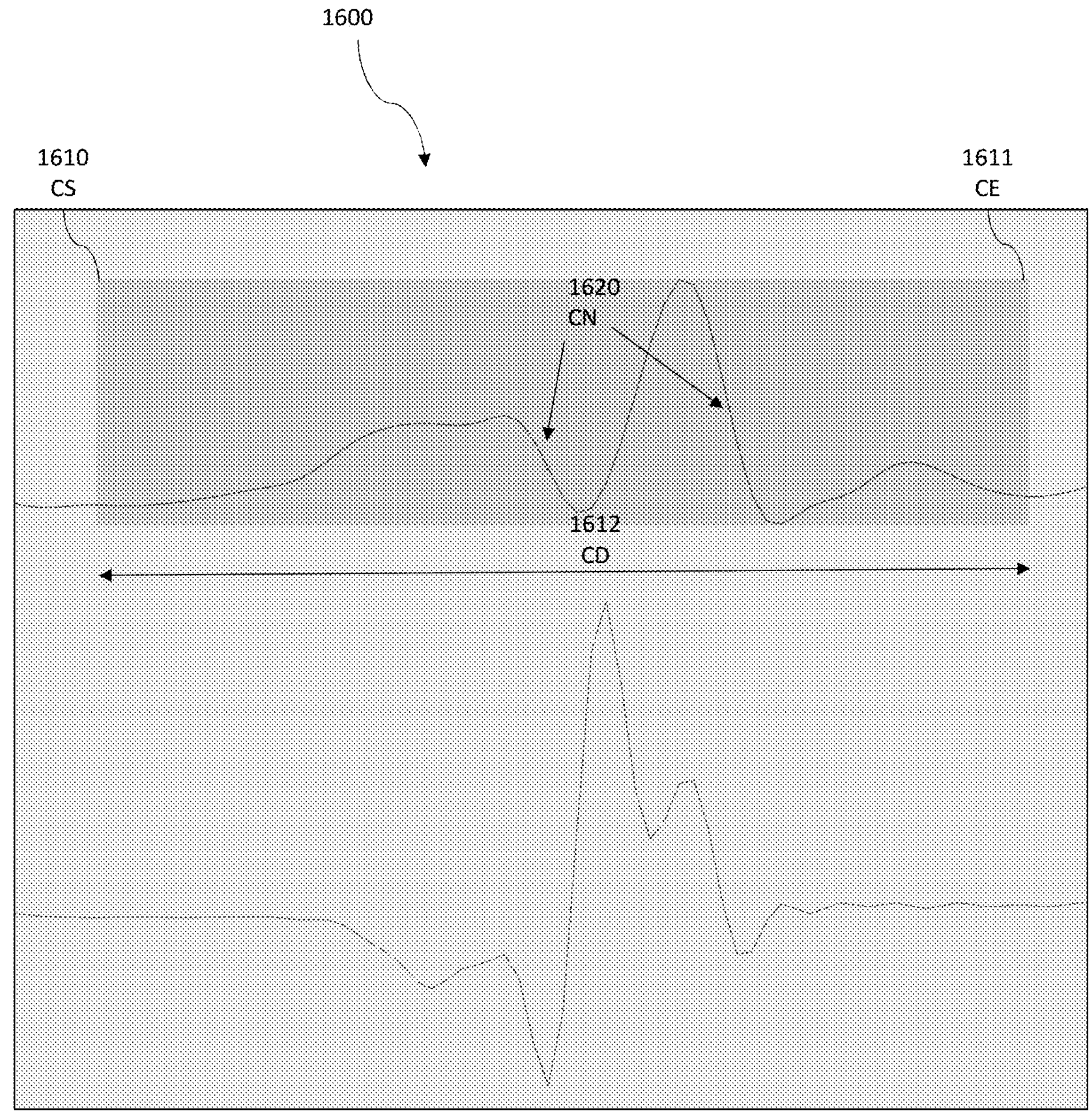
FIG. 16 is an example of a unipolar electrogram annotated with determined complex level parameters.

FIG. 16 is an example complex 1600 of a unipolar electrogram annotated with determined complex level parameters. In the example illustrated in FIG. 16, the unipolar electrogram complex 1600 is annotated with the complex start (CS) 1610 (the start of the bipolar activity window), the complex end (CE) 1611 (the end of the bipolar activity window), and the complex duration (CD) 1612. The number of slopes (CN) 1620 and respective slope amplitude (CA) and slope value (CV) may be determined. These parameters may be used to calculate a complex amplitude ratio (CAR) and a complex slope ratio (CSR). For example, CAR may be calculated using Equation 1, below, where min(CA) is the minimum amplitude and max(CA) is the maximum amplitude. Similarly, CSR may be calculated using Equation 2, below, where min(CV) is the minimum slope value and max(CV) is the maximum slope value of the slopes within the activity window. The fractionation analysis may take the complex level parameters into account, as discussed in more detail below.

$$CAR = \frac{\min(CA)}{\max(CA)} \quad \text{Eq. 1}$$

$$CSR = \frac{\min(CV)}{\max(CV)} \quad \text{Eq. 2}$$

Figures 17A, 17B, 17C:
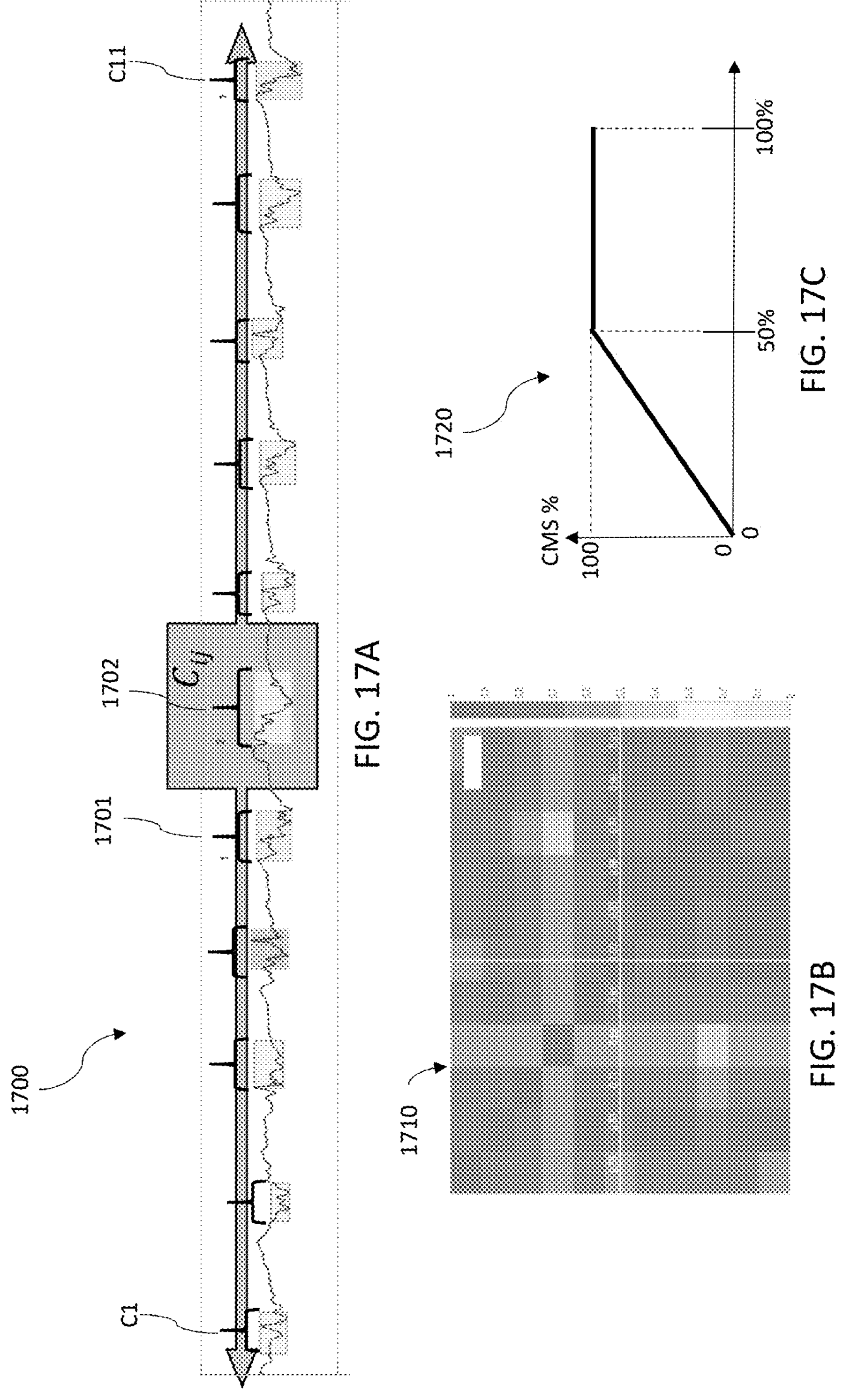
FIG. 17A is an example of a slope cardiogram analyzed for downstroke cross correlation between complexes of all bipolar activity window signals in the same unipolar electrogram.
FIG. 17B is a cross-correlation matrix illustrating the correlation between every possible pair of complexes in the example unipolar electrogram of FIG. 17A.
FIG. 17C is a graph illustrating a complex morphological stability (CMS) score, according to an exemplary embodiment.

With reference to FIG. 17A, an example slope cardiogram is analyzed for down slope cross correlation between all complexes C1 to C11 in the same unipolar electrogram 1700. The correlation of an ith complex 1701 with a jth complex 1702 may be denoted as $C_{ij}$, with the value of $C_{ij}$ ranging from 1 to 0. A $C_{ij}$ value of 1 indicates that the two complexes are identical and a $C_{ij}$ value of 0 indicates that there is no correlation between the two complexes. A correlation value greater than 0 to other complexes provides an indication that the present signal is not just noise. The correlation may be determined using the morphology of two complexes. In other embodiments, correlation is determined using the timing of slopes within the complexes. The timing of slopes is not affected by respiration, blood flow, etc., which may affect the morphology of a complex.

FIG. 17B is a cross-correlation matrix 1710 graphically illustrating the correlation of complexes between every possible pair of the 11 complexes C1-C11$s$ in the example unipolar electrogram 1700 of FIG. 17A. In FIG. 17B, the higher the correlation value between a pair, the darker the box representing the pair is shaded. For example, boxes representing pairs with correlation values 0.85-1 are most darkly shaded. As can be seen by the correlation matrix 1710, the complexes of the example unipolar electrogram 1700 are highly correlated.

In embodiments where correlation is determined using morphology, a complex morphological stability (CMS) may be calculated. CMS may be calculated using Equation 3, below, where XTC is a threshold correlation value. In one example, the threshold correlation value is 0.8 and if half of the complexes show high correlation, the CMS score is 100, as illustrated in FIG. 17C.

$$CMS_i = 100 * \left(\sum_{j=1}^{n} (C_{ij} > XTC) - 1\right) \Big/ (n-1) \quad \text{Eq. 3}$$

where n is the number of complexes over which the determination is made. In the example of FIG. 17A, that number is eleven. The fractionation analysis may consider a unipolar electrogram signal's CMS value, as discussed in more detail below.

Additionally, local activation time (LAT) of a significant unipolar slope may be calculated. The LAT of the electrical activity of at a desired location may be defined in terms of the electrical activity satisfying a predefined condition. For example, the predefined condition may comprise a time of occurrence of the largest rapid deflection of the electrogram at the location, and the LAT is assumed to be the time from reference instance to the following onset of the largest rapid deflection of the electrogram of the location. In case of no clear largest rapid deflection, the mid-amplitude or mid-time point may be used as the LAT.

LAT may be positive or negative. Methods for determining the time of occurrence of the largest rapid deflection of the electrogram, and other definitions and conditions for determining the LAT, will be familiar to those skilled in the art, and all such methods, definitions, and conditions are assumed to be comprised within the scope of the present invention.

Figure 18:
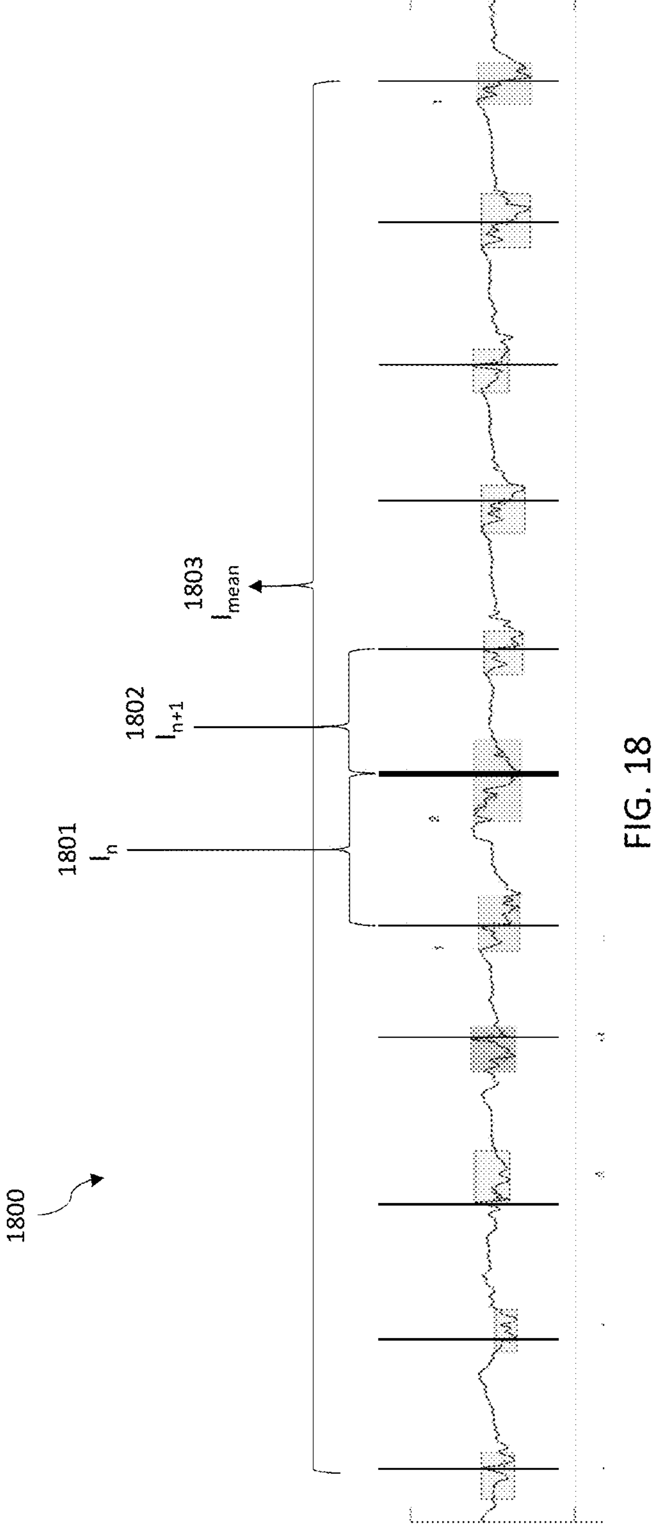
FIG. 18 is an example of a unipolar electrogram where the time intervals of a bipolar electrogram are calculated and compared to each other.

FIG. 18 is an example of a unipolar electrogram 1800 where the time intervals of unipolar complexes within bipolar activity windows (indicated with shading) are calculated and compared to each other, according to an embodiment. For example, a time interval (In) 1801 between the LAT of successive unipolar electrogram complexes within the respective bipolar activity windows may be calculated and compared to a next time interval ($I_{n+1}$) 1802 that follows the time interval 1801. A mean time interval ($I_{mean}$) 1803 of time intervals of a unipolar electrogram over a predetermined number of intervals that contain time interval ($I_n$) 1801 and time interval ($I_{n+1}$) 1802 may also be calculated to determine a complex timing stability (CTS) value.

For example, if Equation 4 is satisfied, then the CTS value is 0. If Equation 5a is satisfied, then Equation 5b may be used to calculate the CTS value.

$$\max(I_n - I_{mean}, I_{n+1} - I_{mean}) > 2 * I_{mean} \quad \text{Eq. 4}$$

$$\max(I_n - I_{mean}, I_{n+1} - I_{mean}) \leq 2 * I_{mean} \quad \text{Eq. 5a}$$

$$CTS = 100 * \left(1 - \frac{\text{abs}(\max(I_n - I_{mean}, I_{n+1} - I_{mean}))}{I_{mean}}\right) \quad \text{Eq. 5b}$$

The fractionation analysis may take the CTS value into account, as discussed in more detail below.

Figure 19:
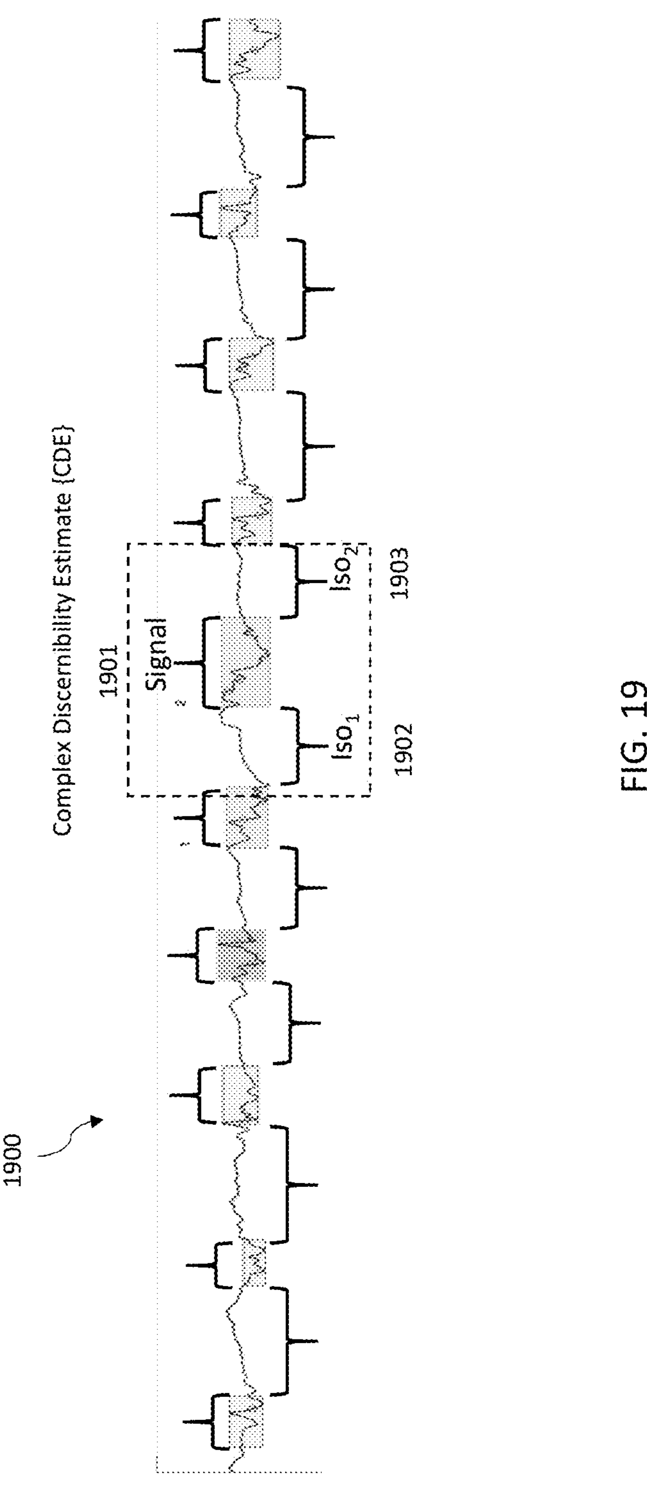
FIG. 19 is an example of a unipolar electrogram illustrating a complex discernibility estimate (CDE) calculation.

FIG. 19 is an example of a unipolar electrogram 1900 illustrating a complex discernibility estimate (CDE) calculation. Portions indicated with the upper brackets of the unipolar electrogram within a bipolar activity window are complexes, such as complex 1901, and portions of the electrogram outside of the bipolar activity window are designated with lower brackets as isoelectric intervals. An isoelectric interval $Iso_1$ 1902 may be compared to a next isoelectric interval $Iso_2$ 1903. If the isoelectric intervals 1902, 1903 surrounding the complex 1901 are highly comparable to the signal of complex 1901, then the complex 1901 has a low CDE, which is not desirable. CDE using the root mean square (RMS) amplitudes of the electrogram portions per Equation 6. The fractionation analysis may take the CDE value into account, as discussed in more detail below.

CDE=100*RMS(Signal of Complex)/RMS(Signal of Complex+Iso1+Iso2) Eq.6

The processor of the computing device 22 may be configured use the received and/or location signals to calculate measurement changes in the location of the catheter 14 during the collection of signals. Measurement computations may account for respiratory movement when measuring changes in the location of the catheter 14 sensors. Position stability refers to the measurement of changes in the location of the distal end of the catheter 14 during the collection of signals. In some embodiments, the fractionation analysis may require that the variation of the location of the catheter over a defined time window be not greater than a predefined maximum distance. The variation may be measured in terms of standard deviation about the mean position during the defined time window.

A Tissue Proximity Indicator (TPI) value can indicate whether a catheter was in proximity to the tissue of interest when a signal was recorded. The TPI may be positive or negative and may indicate whether the catheter is in proximity to tissue, not in proximity to tissue, or if it is unknown. Generally, for accuracy, signals taken when the catheter is in contact with or in proximity to tissue are preferable. Additionally, if the distal end of the catheter 14 is touching the tissue, the signal may indicate characteristics of the tissue. The fractionation analysis may or may not take a TPI value of a signal into account. For example, if the TPI indicates that a signal was not recorded within a certain proximity, then the analysis may not use that signal in the fractionation analysis.

Also, slope ensemble statistics may be calculated from slope characteristics per complex, per potential type. For example, if there is a single potential within a bipolar activity window of a unipolar electrogram, the amplitude and slope may be determined. If there is a double potential, a fractionated potential (three deflections) or a highly fractionated potential (long and more than three deflections) within a bipolar activity window, the mean amplitude and slope may be determined. In some complexes, there may be a slope that does not meet a minimum amplitude or other characteristic within a complex so that it is not counted in determining potential type. For example, a complex having three slopes, where one slope is not of a predetermined minimum amplitude, that complex can be considered as having a double potential.

The slope amplitude and value ensemble statistics may be sorted from lowest to highest to create scales AREST and VREST. The rating of a maximum amplitude AREST(CA)

and slope VREST(CV) may be determined per complex in sorted lists by finding the index>REST(AREST,VREST) divided by the number of entries in the list per potential type.

Slope amplitude and slope value may be rated based on potential dedicated scales. The score of amplitude may be determined per complex in ASCALE(CA) and VSCALE (CV) within the dedicated scales, by finding an index divided by the number of entries in the list per potential type.

Figure 20:
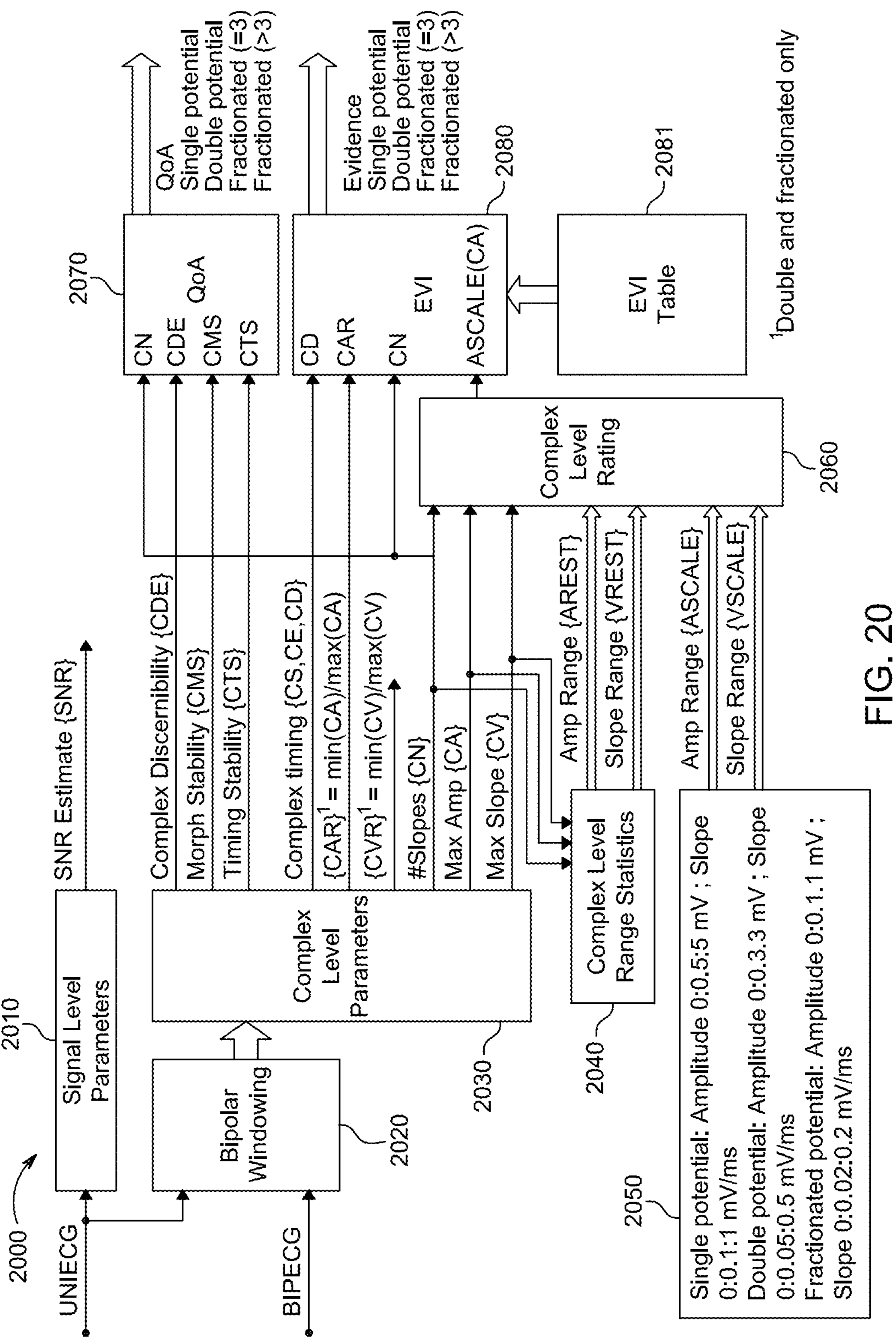
FIG. 20 is a flow chart diagram of the fraction detection analysis, according to an exemplary embodiment.

FIG. 20 is a flow chart diagram of an example fractionation analysis 2000. The analysis 2000 makes a quality of annotation (QoA) measurement and evidence value (EVI) measurement. The QoA is a level of confidence provided per annotation. The QoA may be based on complex parameters within a recording and provided per complex type. The EVI is annotation evidence provided per complex (bipolar activity window). In this example, the evidence annotation value is based on slope parameters within a complex and provided per complex type.

At 2010, one or more signal level parameters of a unipolar electrogram are determined. The one or more signal level parameters may include, but is not limited to, an SNR estimate. The SNR estimate may be performed according to the methods described above.

At 2020, a bipolar activity window of a bipolar electrogram is determined. The bipolar activity window may be determined using the methods described above.

At 2030, one or more complex level parameters are determined based on the bipolar activity window. As illustrated in FIG. 20, the one or more complex parameters may include complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV). A unipolar/bipolar slope overlap (UBO) parameter may also be determined. The complex level parameters may be determined using the methods described above.

At 2040, the number of slopes (CN), maximum amplitude (CA), and maximum slope (CV) may be used to determine one or more complex level range rating statistics. The one or more complex level range rating statistics may include, but are not limited to a relative slope amplitude range (AREST) and slope value range (VREST). The relative slope amplitude range (AREST) and slope value range (VREST) may be determined using the methods described above. Additionally, or alternatively, at 2050, an absolute slope amplitude range (ASCALE) and slope value range (VSCALE) relative to AREST and VREST may be determined. In the embodiment illustrated in FIG. 20, example potential dedicated scales for slope amplitude and slope value for a single potential, double potential, and fractionated potential are shown with highly fractionated potential included in the listing for fractionated potential. The example dedicated scales are also provided below in Table 1 below.

TABLE 1

| | Amplitude | Slope |
|---|---|---|
| Single potential | 0:0.5:5 mV | 0:0.1:1 mV/ms |
| Double potential | 0:0.3:3 mV | 0:0.05:0.5 mV/ms |
| Fractionated potential | 0:0.1:1 mV | Slope 0:0.02:0.2 mV/ms |

At 2060, complex level rating scores may be determined. The complex level rating scores may be determined using the methods described above. For example, in some embodiments, the rating of a maximum amplitude AREST(CA) and slope SREST(CV) may be determined per complex in sorted lists by finding the index>REST(AREST,VREST) divided by the number of entries in the list per potential type.

Figure 21:
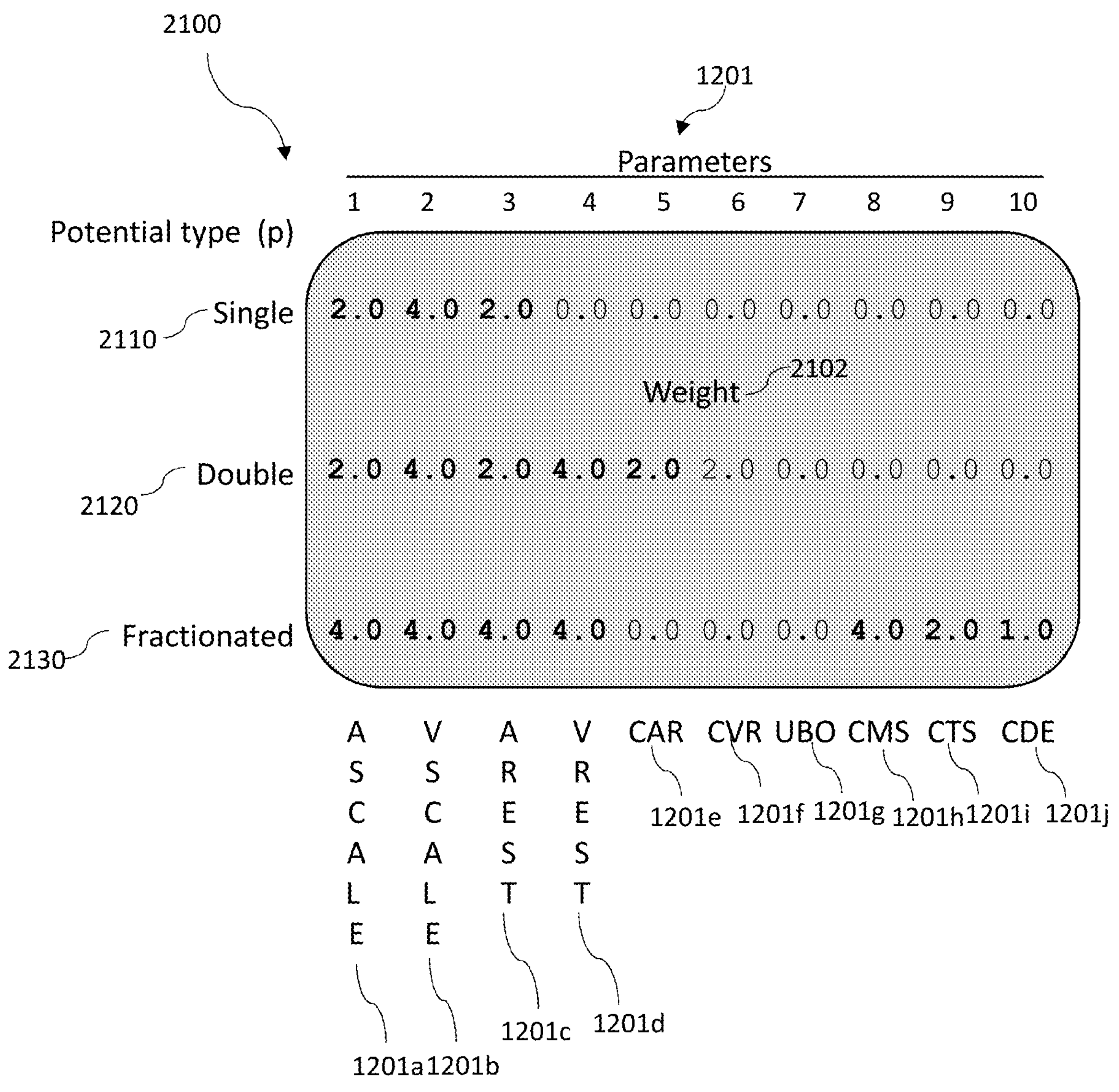
FIG. 21 is a diagram illustrating parameters and weights for a quality of annotation (QoA) measurement, according to an exemplary embodiment.

At 2070, the QoA is then determined based on one or more complex level parameters and/or complex level ratings at 2060, as discussed in more detail with respect to FIG. 21. At 2080 the evidence annotation measurement EVI is determined using an evidence table 2081, as discussed in more detailed with respect to FIG. 22.

FIG. 21 is a diagram 2100 illustrating parameters 2101 and weights 2102 for a QoA measurement, according to an embodiment. In some embodiments, the QoA measurement may be the weighted sum of two or more following parameters: (1) ASCALE 2101*a*; (2) VSCALE 2101*b*; (3) AREST 2101*c*; (4) VREST 2101*d*; (5) complex amplitude ratio (CAR) 2101*e*; (6) complex slope ratio (CVR) 2101*f*; (7) unipolar/bipolar slope overlap (UBO) 2101*g*; (8) complex morphological stability (CMS) 2101*h*; (9) complex timing stability (CTS) 2101*i*; and (10) complex discernibility estimate (CDE) 2101*j*. However, this list of parameters is not exhaustive, and other parameters may be used in the QoA measurement.

The weights used in the QoA measurement may be defined per potential type. For example, the weight may be defined depending on whether the potential type is single 2110, double 2120, or fractionated 2130. In this example, fractionated value is used for highly fractionated types as well.

In one example, the QoA measurement is calculated as a percentage using Equation 7, below, using the 10 parameters listed above (N=10). However, more or less parameters may be utilized in the QoA measurement.

$$QoA = 100 * \left(\sum_{i=1}^{N} P_i * w_{p,i}\right) \Big/ \sum w_{pi} \qquad \text{Eq. 7}$$

where N is the number of parameters, $P_i$ is the value of the ith of the N parameters listed above, $w_{p,i}$ is the weight value for the ith parameter depending on potential type (p) from the table of FIG. 21.

Figure 22:
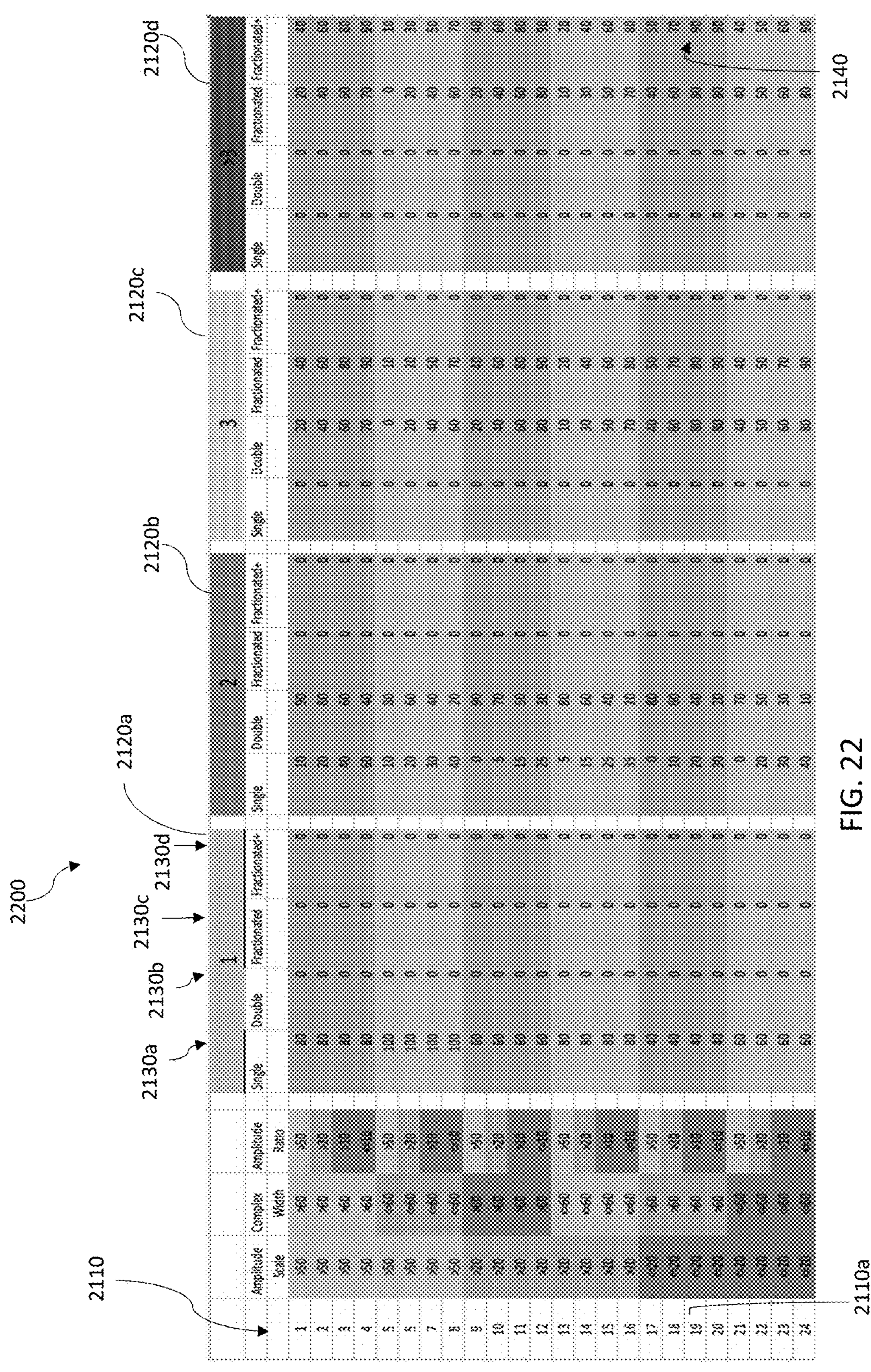
FIG. 22 is a classification table of evidence annotation measurement (EVI) showing likelihood of a bipolar activity window having detected activation with respect to respective number of slopes and potential types.

FIG. 22 is an example evidence table 2200 for the evidence annotation measurement EVI as a percentage value, according to an embodiment. The evidence table may comprise a plurality of classifications 2110 based one or more ECG complex parameters. In the example illustrated in FIG. 22, the classifications 2110 are based on ECG complex amplitude scale, complex width, and amplitude ratio of a signal. For example, a complex with an amplitude scale of less than or equal to 20, a complex width of greater than 60, and amplitude ratio of greater than 10 may be classified as Group 19 (2110*a*). An evidence score may then be coded in the table based on the classification, number of slopes (one 2120*a*, two 2120*b*, three 2120*c*, or more than three 2120*d*), and potential type (i.e., single 2130*a*, double 2130*b*, fractionated 2130*c* or highly fractionated (fractionate+) 2130*d*). For example, if complex classified as Group 19 has more than three slopes and was identified as a highly fractionated potential, then the complex has an evidence score of 90 (2140) (if identified as a fractionated potential, then the complex has an evidence score of 80).

The QoA and EVI measurements may be used to determine a final score for a complex. In one example, a modulating factor M is first calculated based on the QoA and EVI. In this example, the modulating factor (M) is determined using Equation 8.

$$M=\left[2*\left(1-\frac{EVI}{100}\right)*QoA\right]+(EVI-100) \quad \text{Eq. 8}$$

Then the final score S is calculated as the sum of the evidence score EVI and the modulating factor M, as demonstrated in Equation 9.

$$S=\text{EVI}+M \quad \text{Eq. 9}$$

Figure 23:
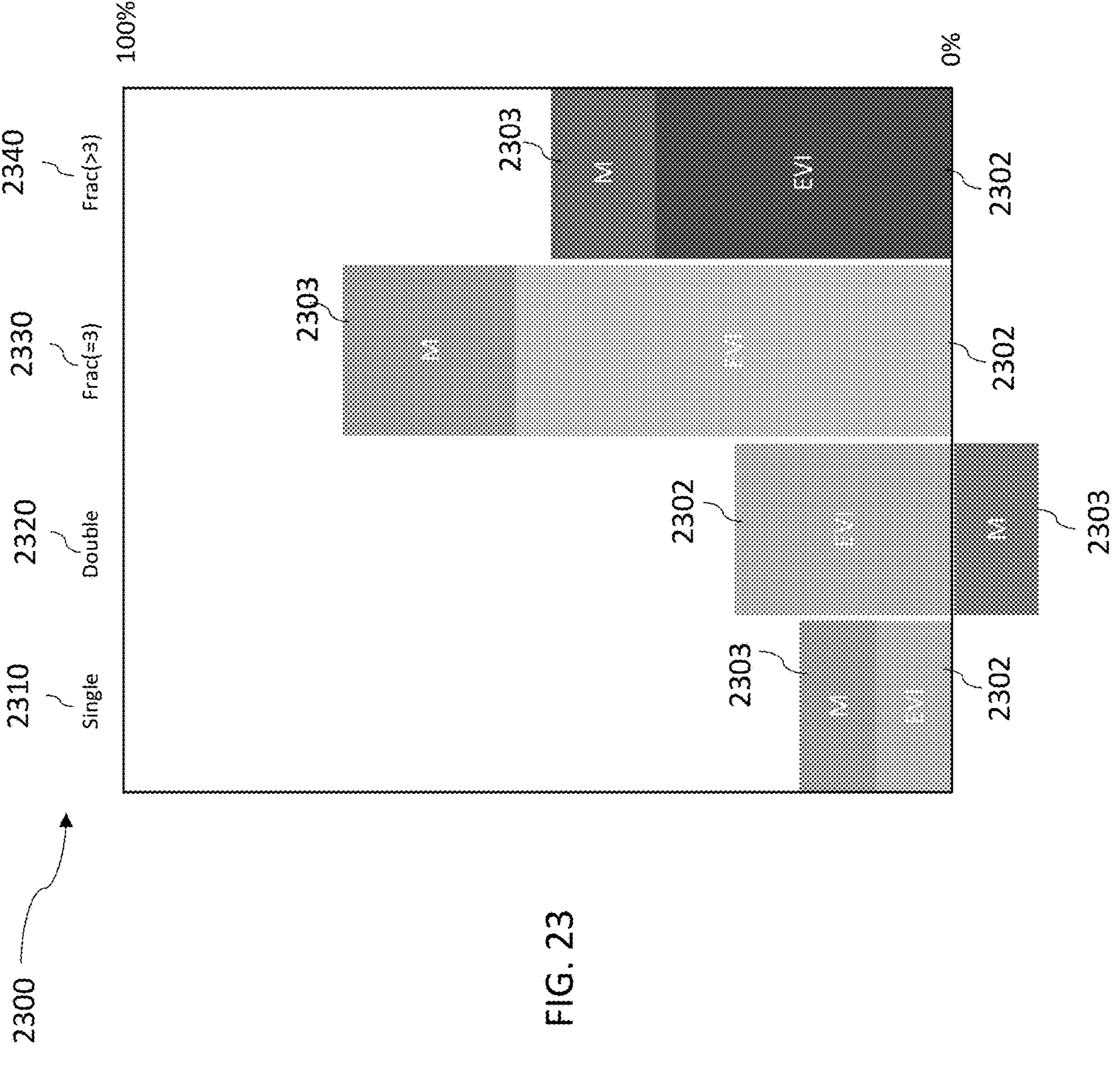
FIG. 23 is a graph illustrating a combined evidence annotation measurement and quality factor percentages for a single potential, a double potential, a fractionated potential (3 deflections), and a highly fractionated potential (>3 deflections) according to an exemplary embodiment

FIG. 23 is a graph 2300 illustrating a combined evidence annotation measurement (EVI) and modulating factor M for a single potential 2310, a double potential 2320, a fractionated potential (three deflections) 2330 and a highly fractionated potential (long and more than three deflections) 2340, according to an embodiment. As shown in FIG. 23, the final score may be expressed as a percentage, with 100 percent being the highest possible score. The final score may be used to determine whether a complex is a fractionated complex.

A unipolar electrogram having a predetermined number of successive complexes with final scores of 90% or higher may be identified as a fractionated signal. For example, unipolar electrogram complexes with an EVI value of 90% from the FIG. 22 table and a QoA value of at least 50% as well as unipolar electrogram complexes with an EVI value of 80% from the FIG. 22 table and a QoA value of at least 75% meet this final score threshold of 90% or higher.

Detection of fractionated potentials is relevant in combination with LAT to create a view of propagation of waves during an arrhythmia such as atrial flutter. Fractionated potentials may occur as a result of slow propagation of activation waves, travelling across areas of diseased tissue that may show an erratic (e.g. zig-zag) type of activation slowing down propagation compared to straightforward fast propagation in healthy tissue (structural fractionation).

In addition, double and fractionated potential may occur as a result of multiple dissociated waves separated by functional lines of block that also results in complex activation patterns and associated fractionated potentials (functional fractionation). The latter, in general, does not persist very long, so persistent fractionation (e.g. over at least several beats) points to the structural nature of fractionation.

Accordingly, detection of persistent fractionated potentials, in combination with local activation times (LATs) derived from single and double potentials allows for the creation of an activation map including demarcation of potential sites of ablation appointed by fractionated potentials.

A cardiac tissue region that is highly correlated with fractionated signals may be determined by the apparatus 10 as an arrhythmogenic site for treatment via catheter ablation. For example, unipolar electrograms representing an area of study such as the entirety of a left atrium may be obtained from the catheter 47 and scored by computing device 22 based on the above. The unipolar electrograms scored as fractionated signals are evaluated to determine if there is an atrial tissue area, represented by at least several (e.g. >3) replicated fractionated unipolar potentials. An atrial tissue area meeting having a predetermined number of unipolar electrograms that meet such criteria, for example, at least three, is then determined by the processor of the computing device 22 to be an atrial arrhythmogenic site for potential ablation treatment. The area of study with the determined atrial arrhythmogenic site can then be displayed on the display 29 to assist the operator 16 in performing an ablation treatment.

For reduced computation, a more focused study may be conducted. For example, in lieu of evaluating unipolar electrograms representing the entirety of a heart chamber, unipolar electrograms representing a cardiac region surrounding or within a low voltage area can be obtained and scored to determine the existence of a cardiac tissue area within the cardiac region of study that meets the above criteria to be determined to be an arrhythmogenic site for potential ablation treatment.

The methods described herein may comprise algorithms that can be utilized by a skilled software engineer to generate the requisite step-by-step computer codes for implementation of the overall method in a computer system (e.g., a general-purpose computer or a special purpose computer such as the Carto system). The corresponding electrograms, calculations and results may be displayed on a display, such as a graphical user interface.

It should be understood that many variations are possible based on the disclosure herein. Although features and elements are described above in particular combinations, each feature or element can be used alone without the other features and elements or in various combinations with or without other features and elements.

What is claimed is:

1. A medical apparatus for improved detection of fractionated signals for site determination of cardiac arrhythmias within a heart of a subject comprising:

a catheter component including at least one catheter having a plurality of selectively locatable distal end sensors and electrodes coupled to a computing device;

the sensors configured to sense (ECG) signals within the subject's heart;

the computing device having a processor and associated memory;

the computing device configured to receive, record and process electrocardiogram (ECG) signals in the form of bipolar and unipolar ECGs associated with respective cardiac tissue locations based on sensing locations of respective distal end sensors;

with respect to a cardiac tissue area of study for which unipolar ECGs are recorded that include signals from a plurality of successive heartbeats corresponding to locations within the cardiac tissue area of study, the processor configured to detect the fractionated signals comprising Fractionated Unipolar ECG Signal Complexes (FUESCs) from among the unipolar ECGs by:

determining bipolar activity windows from a bipolar ECG comprising a first unipolar ECG and a second unipolar ECG and defining a series of complexes of the first unipolar ECG that each correspond to a respective bipolar activity window;

determining a plurality of complex level parameters with respect to the complexes of the first unipolar ECG with respect to a plurality of successive bipolar activity windows;

calculating a plurality of complex level ratings based on at least one of the plurality of complex level parameters;

calculating a quality of annotation measurement (QoA) with respect to the complexes of the first unipolar ECG using a plurality of parameters that include at least one of the plurality of complex level parameters and at least one of the plurality of complex level ratings;

determining an evidence annotation measurement (EVI) with respect to the complexes of the first unipolar ECG using at least one of the plurality of complex level parameters and at least one of the plurality of complex level ratings; and calculating a final score with respect to the complexes of the first unipolar ECG based on the QoA and the EVI of each complex such that a complex of the first unipolar ECG is determined to be a FUESC upon a condition that its final score is at least a predetermined threshold; and wherein the FUESCs are automatically identified, based upon the detection of the fractionated signals, for the site determination of the cardiac arrhythmias for treatment by ablation, as a cardiac tissue site that includes respective locations corresponding to a predetermined number of unipolar ECGs that include a predetermined number of FUESCs, and responsive to the determination of said cardiac tissue site, controlling and delivering ablation energy to the cardiac tissue site via the catheter.

2. The apparatus of claim 1 further comprising a display coupled with the computing device wherein:

the processor is configured to output to the display a visualization of the cardiac tissue area of study of the subject's heart including one or more of the following:

the relative locations of the distal end sensors with respect thereto along with selected sensed ECGs received by at least one of the distal end sensors;

a visual indication of cardiac tissue determined to be cardiac arrhythmia sites for treatment by ablation; and a colorization of the cardiac tissue based on selected criteria.

3. The apparatus of claim 1, wherein the processor is configured to determine the bipolar activity windows by determining a first activity window and a second activity window and fusing the first activity window and the second activity window on a condition that they overlap by 20 percent or more.

4. The apparatus of claim 1, wherein:

the unipolar ECGs include signals from at least ten successive heartbeats;

the cardiac tissue area of study is atrial tissue of at least a portion of an atrial chamber of the subject's heart;

the plurality of complex level parameters within the bipolar activity window that the processor is configured to determine are selected from a group consisting of: complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV); and the processor is configured to determine an atrial cardiac arrhythmia site for treatment by ablation as an atrial tissue site that includes respective locations corresponding to at least three unipolar ECGs that include at least three successive of FUESCs.

5. The apparatus of claim 4, wherein the processor is configured to calculate the plurality of complex level ratings using parameters selected from a group consisting of: number of slopes (CN), maximum amplitude (CA), maximum slope (CV), relative amplitude range (AREST), relative slope range (VREST), absolute amplitude range (ASCALE), and absolute slope range (VSCALE).

6. The apparatus of claim 5, wherein the processor is configured to calculate the QoA based on at least two parameters of the group consisting of: ASCALE, VSCALE, AREST, VREST, CAR, CVR, unipolar/bipolar slope overlap (UBO), CMS, CTS, and CDE.

7. The apparatus of claim 6, wherein the processor is configured to determine a potential type of the complexes of the first unipolar electrogram as either a single potential, a double potential, a fractionated potential or a highly fractionated potential.

8. The apparatus of claim 7, wherein the processor is configured to calculate QoA with respect to the complexes of the first unipolar ECG based on the formula:

$$QoA = 100 * \left(\sum_{i=1}^{N} P_i * w_{p,i}\right) \Big/ \sum w_{pi}$$

where N is the number of parameters, $P_i$ is the value of the ith of the N parameters listed above, $w_{p,i}$ is a weight value for the ith parameter depending on a potential type p.

9. The apparatus of claim 7, wherein the processor is configured to calculate the final score with respect to the complexes of the first unipolar ECG as a percentage of the sum of EVI plus M, where EVI is determined as a percentage based on a table entry corresponding to an amplitude scale, complex width, and amplitude ratio classification and a number of slopes and the potential type of the first unipolar ECG and M is calculated as a percentage value based on the formula:

$$M = \left[2 * \left(1 - \frac{EVI}{100}\right) * QoA\right] + (EVI - 100).$$

10. A method for improved detection of fractionated signals for site determination of cardiac arrhythmias within a heart of a subject comprising:

receiving, recording, and processing electrocardiogram (ECG) signals in the form of bipolar and unipolar ECGs associated with respective cardiac tissue locations based on sensing locations of respective distal end sensors and electrodes of a catheter;

with respect to a cardiac tissue area of study for which unipolar ECGs are recorded that include signals from a plurality of successive heartbeats corresponding to locations within the cardiac tissue area of study, detecting the fractionated signals comprising Fractionated Unipolar ECG Signal Complexes (FUESCs) from among the unipolar ECGs by:

determining bipolar activity windows from a bipolar ECG comprising a first unipolar ECG and a second unipolar ECG and defining a series of complexes of the first unipolar ECG that each correspond to a respective bipolar activity window;

determining a plurality of complex level parameters with respect to the complexes of the first unipolar ECG with respect to a plurality of successive bipolar activity windows;

calculating a plurality of complex level ratings based on at least one of the plurality of complex level parameters;

calculating a quality of annotation measurement (QoA) with respect to the complexes of the first unipolar ECG using a plurality of parameters that include at least one of the plurality of complex level parameters and at least one of the plurality of complex level ratings;

determining an evidence annotation measurement (EVI) with respect to the complexes of the first unipolar ECG using at least one of the plurality of complex level parameters and at least one of the plurality of complex level ratings; and calculating a final score with respect to the complexes of the first unipolar ECG based on the QoA and the EVI of each complex such that a complex of the first unipolar ECG is determined to be a FUESC upon a condition that its final score is at least a predetermined threshold; and wherein the FUESCs are automatically identified, based upon the detection of the fractionated signals, for the site determination of the cardiac arrhythmias for treatment by ablation, as a cardiac tissue site that includes respective locations corresponding to a predetermined number of unipolar ECGs that include a predetermined number of FUESCs, and responsive to the determination of said cardiac tissue site, controlling and delivering ablation energy to the cardiac tissue site via the catheter.

11. The method of claim 10 further comprising displaying a visualization of the cardiac tissue area of study of the subject's heart including one or more of the following:

the relative locations of the distal end sensors with respect thereto along with selected sensed ECGs received by at least one of the distal end sensors;

a visual indication of cardiac tissue determined to be cardiac arrhythmia sites for treatment by ablation; and a colorization of the cardiac tissue based on selected criteria.

12. The method of claim 10, wherein the determining the bipolar activity windows includes determining a first activity window and a second activity window and fusing the first activity window and the second activity window on a condition that they overlap by 20 percent or more.

13. The method of claim 10 conducted with respect to unipolar ECGs that include signals from at least ten successive heartbeats and a cardiac tissue area of study that is atrial tissue of at least a portion of an atrial chamber of the subject's heart wherein:

the plurality of complex level parameters within the bipolar activity window that are determined are selected from a group consisting of: complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV); and an atrial cardiac arrhythmia site for treatment by ablation is determined as an atrial tissue site that includes respective locations corresponding to at least three unipolar ECGs that include at least three successive of FUESCs.

14. The method of claim 13, wherein the plurality of complex level ratings are calculated using parameters selected from a group consisting of: number of slopes (CN), maximum amplitude (CA), maximum slope (CV), relative amplitude range (AREST), relative slope range (VREST), absolute amplitude range (ASCALE), and absolute slope range (VSCALE).

15. The method of claim 14, wherein the QoA is calculated based on at least two parameters of the group consisting of: ASCALE, VSCALE, AREST, VREST, CAR, CVR, unipolar/bipolar slope overlap (UBO), CMS, CTS, and CDE.

16. The method of claim 15, wherein a potential type of the complexes of the first unipolar electrogram is determined as either a single potential, a double potential, a fractionated potential or a highly fractionated potential.

17. The method of claim 16, wherein QoA with respect to the complexes of the first unipolar ECG are calculated based on the formula:

$$QoA = 100 * \left(\sum_{i=1}^{N} P_i * w_{p,i}\right) \Big/ \sum w_{pi}$$

where N is the number of parameters, $P_i$ is the value of the ith of the N parameters listed above, $w_{p,i}$ is a weight value for the ith parameter depending on a potential type p.

18. The method of claim 17, wherein the processor is configured to calculate the final score with respect to the complexes of the first unipolar ECG as a percentage of the sum of EVI plus M, where EVI is determined as a percentage based on a table entry corresponding to an amplitude scale, complex width, and amplitude ratio classification and a number of slopes and the potential type of the first unipolar ECG and M is calculated as a percentage value based on the formula:

$$M = \left[2 * \left(1 - \frac{EVI}{100}\right) * QoA\right] + (EVI - 100).$$

19. A tangible non-transitory computer-readable medium in which program instructions are stored for improved detection of fractionated signals for site determination of cardiac arrhythmias, which, when read by a processor, cause the processor to:

process electrocardiogram (ECG) signals in the form of bipolar and unipolar ECGs associated with respective cardiac tissue locations based on sensing locations of respective distal end sensors and electrodes of a catheter;

with respect to unipolar ECGs of a cardiac tissue area of study that include signals from a plurality of successive heartbeats corresponding to locations within the cardiac tissue area of study, detect the fractionated signals comprising Fractionated Unipolar ECG Signal Complexes (FUESCs) from among the unipolar ECGs by:

determining bipolar activity windows from a bipolar ECG comprising a first unipolar ECG and a second unipolar ECG and defining a series of complexes of the first unipolar ECG that each correspond to a respective bipolar activity window;

determining a plurality of complex level parameters with respect to the complexes of the first unipolar ECG with respect to a plurality of successive bipolar activity windows;

calculating a plurality of complex level ratings based on at least one of the plurality of complex level parameters;

calculating a quality of annotation measurement (QoA) with respect to the complexes of the first unipolar ECG using a plurality of parameters that include at least one of the plurality of complex level parameters and at least one of the plurality of complex level ratings;

determining an evidence annotation measurement (EVI) with respect to the complexes of the first unipolar ECG using at least one of the plurality of complex level parameters and at least one of the plurality of complex level ratings; and calculating a final score with respect to the complexes of the first unipolar ECG based on the QoA and the EVI of each complex such that a complex of the first unipolar ECG is determined to be a FUESC upon a condition that its final score is at least a predetermined threshold; and a wherein the FUESCs are automatically identified, based upon the detection of the fractionated signals, for the site determination of the cardiac arrhythmias for treatment by ablation, as a cardiac tissue site that includes respective locations corresponding to a predetermined number of unipolar ECGs that include a predetermined number of FUESCs, and responsive to the determination of said cardiac tissue site, controlling and delivering ablation energy to the cardiac tissue site via the catheter.

20. The tangible non-transitory computer-readable medium of claim 19 wherein the program instructions, which, when read by a processor, cause the processor to:

identify FUESCs from among the recorded unipolar ECGs with respect to unipolar ECGs that include signals from at least ten successive heartbeats and a cardiac tissue area of study that is atrial tissue of at least a portion of an atrial chamber of the subject's heart;

determine the plurality of complex level parameters within the bipolar activity window selected from a group consisting of: complex discernibility (CDE), complex morphological stability (CMS), complex timing stability (CTS), bipolar activity window start (CS), bipolar activity window end (CE), and bipolar activity window duration (CD), minimum/maximum amplitude ratio (CAR), minimum/maximum slope ratio (CVR), number of slopes (CN), maximum slope amplitude (CA), and maximum slope (CV);

calculate the plurality of complex level ratings using parameters selected from a group consisting of: number of slopes (CN), maximum amplitude (CA), maximum slope (CV), relative amplitude range (AREST), relative slope range (VREST), absolute amplitude range (ASCALE), and absolute slope range (VSCALE);

calculate the QoA based on at least two parameters of the group consisting of: ASCALE, VSCALE, AREST, VREST, CAR, CVR, unipolar/bipolar slope overlap (UBO), CMS, CTS, and CDE;

determine a potential type of the complexes of the first unipolar electrogram as either a single potential, a double potential, a fractionated potential or a highly fractionated potential; and determine an atrial cardiac arrhythmia site for treatment by ablation is determined as an atrial tissue site that includes respective locations corresponding to at least three unipolar ECGs that include at least three successive of FUESCs.

* * * * *